(12) United States Patent
Rapoport

(10) Patent No.: US 8,308,717 B2
(45) Date of Patent: Nov. 13, 2012

(54) THERMAL ENERGY APPLICATOR

(75) Inventor: Alex Rapoport, Rishon Le Zion (IL)

(73) Assignee: Seilex Ltd, Rishon Le Zion (IL)

( * ) Notice: Subject to any disclaimer, the term of this patent is extended or adjusted under 35 U.S.C. 154(b) by 1389 days.

(21) Appl. No.: 10/577,652

(22) PCT Filed: Jun. 19, 2005

(86) PCT No.: PCT/IL2005/000649
§ 371 (c)(1),
(2), (4) Date: May 1, 2006

(87) PCT Pub. No.: WO2005/122694
PCT Pub. Date: Dec. 29, 2005

(65) Prior Publication Data
US 2008/0287930 A1    Nov. 20, 2008

(51) Int. Cl.
*A61B 18/00* (2006.01)
(52) U.S. Cl. .................. 606/9; 606/5; 607/88; 359/853
(58) Field of Classification Search ................... 606/5, 9;
607/88, 89; 359/853
See application file for complete search history.

(56) References Cited

U.S. PATENT DOCUMENTS

| | | | |
|---|---|---|---|
| 4,167,662 A | 9/1979 | Steen | |
| 4,315,130 A * | 2/1982 | Inagaki et al. | 219/121.6 |
| 4,409,478 A * | 10/1983 | Libby | 250/236 |
| 4,413,180 A * | 11/1983 | Libby | 250/236 |
| 4,518,232 A * | 5/1985 | Dagenais | 359/853 |
| 5,163,936 A | 11/1992 | Black | |
| 5,298,719 A | 3/1994 | Shafir | |
| 5,378,582 A * | 1/1995 | Chan | 430/321 |
| 5,425,727 A * | 6/1995 | Koziol | 606/5 |
| 5,498,508 A * | 3/1996 | Chan | 430/321 |
| 5,582,752 A | 12/1996 | Zair | |
| 5,720,772 A | 2/1998 | Eckhouse | |
| 5,725,522 A | 3/1998 | Sinofsky | |
| 5,743,902 A | 4/1998 | Trost | |
| 6,248,103 B1 | 6/2001 | Tannenbaum et al. | |
| 6,392,683 B1 | 5/2002 | Hayashi | |
| 7,066,929 B1 * | 6/2006 | Azar et al. | 606/9 |
| 2002/0022829 A1 * | 2/2002 | Nagase et al. | 606/12 |
| 2002/0131139 A1 * | 9/2002 | Mandella et al. | 359/215 |
| 2003/0116542 A1 | 6/2003 | McGregor | |
| 2006/0020260 A1 * | 1/2006 | Dover et al. | 606/9 |
| 2006/0058712 A1 * | 3/2006 | Altshuler et al. | 601/15 |
| 2008/0208104 A1 * | 8/2008 | Bragagna et al. | 604/20 |

FOREIGN PATENT DOCUMENTS

| | | |
|---|---|---|
| FR | 2823688 A | 10/2002 |
| GB | 2015813 A | 9/1979 |
| WO | WO 94/07639 A | 4/1994 |

* cited by examiner

*Primary Examiner* — Henry M Johnson, III
*Assistant Examiner* — Jeffrey Lipitz

(57) ABSTRACT

An apparatus and method, for selective thermal treatment of tissue, below the surface, while avoiding injury to the superficial layers of the tissue. The apparatus comprises a reflective beam conversion system for providing a pre-selected therapeutic dose of light energy of optimal spectrum and optimal pulse duration to a confined target volumes at predetermined depth under the tissue surface, while reducing the thermal exposure of the surface of the tissue, and the overlying and surrounding tissues. The method is advantageous for treating a variety of medical and dermatological conditions in a safer and more effective manner.

17 Claims, 14 Drawing Sheets

THERMAL ENERGY APPLICATOR

FIELD OF THE INVENTION

The present invention relates to the field of the application of light energy for thermal treatment below the surface of tissue, while reducing the risk of damage to the surface of the tissue, especially as applied to dermatological thermal treatment.

BACKGROUND OF THE INVENTION

Applying heat is a well-known technique for treating human tissue. Multiple thermal treatment techniques exist for tissue ablation and coagulation as well as for non-ablative tissue stimulation and regeneration. Those techniques include radio-frequency ablation (RFA), microwave, focused ultrasound and lasers. Lasers, and in some cases, other light sources such as intense pulsed light (IPL) sources are especially suitable for the delivery of the required thermal dose to the tissue being treated. Laser radiation energy is measured in Joules (J) and is directly proportional to the quantity of photons of the radiation. Power is the rate of energy exposure measured in Watts (W) where 1 W=1 J/s. Power Density, also known as Irradiance refers to the amount of power per area and is expressed in Watts per centimeter squared (W/cm2). The total amount of energy exposed to a surface is known as the Fluence=Power×Time/Area and is expressed in term of Joules per centimeter squared ($J/cm^2$). In laser surgery, fluence determines the total volume of tissue damage.

In many medical and dermatological applications, the aim of the treatment is to deliver a predetermined amount of thermal energy to a desired target volume of tissue at a specific depth below the surface, while sparing the adjacent and overlying tissue.

One of the disadvantages of prior art laser techniques is its limited ability to deliver significant energy to a desired depth in the tissue, through superficial layers of the tissue, without exposing the superficial layers to significant levels of energy, which can cause undesirable effects to the superficial layers. Moreover, due to tissue attenuation effect, in order for the deeper tissue layers to receive sufficient amount of energy, the superficial layers are exposed to even higher levels of energy thus increasing these undesirable side effects.

Optical scanners have been proposed for addressing problems such as variable depth penetration, non-uniform exposure and consequent charring of tissue surface. In general, prior art scanners, such as those described in U.S. Pat. No. 5,743,902 to Trost, displace an optical treatment beam from one treatment spot to another in a controlled manner. Other scanners such as those described in U.S. Pat. No. 5,582,752 to Zair and U.S. Pat. No. 5,786,924 to Black et al, additionally provide focusing of the beam on the surface using refractive optics (such as lenses) or reflective optics (such as concave and convex mirrors) to provide homogeneous vaporization of the tissue. Although those scanners provide some improvement by allowing more uniform coverage of the surface, they don't address the problem of managing the desired level of energy delivery below tissue surface.

A known technique to address the problem of selective targeting while sparing the adjacent tissues is called Selective Photothermolysis (SP), in which selective tissue thermal damage can be achieved using optical energy with a wavelength that is specifically absorbed by a natural or artificially introduced chromophore in the target area. In addition, the process also involves choosing the duration of the energy pulse to maximize the temperature of the target before significant diffusion of heat to the surrounding tissue can take place. This technique, in the prior art, is limited and is applicable only to applications whereby the treated target has spectral absorption which is different from the adjacent tissue. This isn't the case in many applications.

For example, prior art optical technologies for long-term hair removal treatment are based on thermal destruction of the hair shaft and follicle using wavelengths that are specifically absorbed by the pigment melanin found in the hair follicle. One of the limitations of those technologies is the fact that the epidermis through which the light energy must penetrate is rich in melanin and therefore absorbs a major portion of the energy, resulting in inadequate heating of the hair follicles as well as damage to the epidermis. Using higher energy levels in order to generate sufficient heating of the hair follicles can cause charring and hyper-pigmentation. Although the chromophore being targeted may vary for different applications, the above limitations are common for all such applications.

Another problem with selective photothermolysis is that the wavelength selected for the radiation is generally dictated by the absorption characteristics of the chromophore utilized. However, such wavelengths may not be optimal for penetration deep enough to reach the target due to tissue scattering which depends on wavelength.

Various techniques have been used or proposed to assist in improving the efficiency of the process. These techniques include pre-cooling of the treated area, cooling during the process, selective cooling of the epidermis using millisecond cryogen spray, use of optical transmitting gels to improve coupling into the tissue, convex shaped applicators, and devices to draw folds of skin which may receive radiation from both sides.

Another approach, described in U.S. Pat. No. 5,735,844 to Anderson et al., in International PCT patent application published as WO 98/52481 to Colles and in U.S. patent application Ser. No. 10/033,302 to Anderson et al., use various types of refractive elements such as lenses to focus the optical energy at specific depth under the skin surface, thus increasing the energy fluence at the depth. There are several disadvantages associated with this approach:

1. Optical focusing in the tissue substantially increases the power density of the beam. Such increased power density at a focal point and its immediate proximity is very difficult to control, which may create a serious epidermis safety hazard. This is particularly true with low numerical aperture focusing systems, easily realizable with refractive optics.
2. There can be a significant thermal exposure to overlying tissue located above the target, especially that in close proximity to the target region at the focus.
3. Inability to simultaneously treat multiple, separate targets at different depths using different wavelengths and different light pulse durations.
4. Focusing of the beam using lenses, generally requires contact with the skin surface, which may complicate practical implementation of this method, for example, by precluding use of galvanic scanners.

It must be emphasized that focusing techniques may also lack inherent accuracy and may be dependent on the particular properties of the patient's skin. Scattering of radiation inside the skin may preclude the possibility to attain a well defined focus as well as a well defined treatment depth.

Whereas there may be both advantages and disadvantages to varying degrees in all of these approaches, it is clear that there is a need for an improved light energy delivery system that addresses the problems of sub-surface thermal treatment.

It would therefore be desirable and advantageous to devise an effective method and apparatus for medical and aesthetic thermal treatment of tissue at the desired depth, while minimizing the thermal damage to the overlying layers of the tissue.

Accordingly, it is an object of the present invention to overcome the disadvantages of prior art methods and provide an improved method and apparatus for thermal treatment of a tissue. More specifically, it is an object of the invention to provide an apparatus for thermal treatment of confined tissue volumes at predetermined depths, while minimizing the damage to overlying, superficial tissue layers and surrounding tissues, thus significantly improving the safety of the procedure. Another objective is improving the efficacy of thermal treatment methods by delivering significantly higher fluence levels to the target, than achievable with prior art methods, still preserving safe fluence level at the tissue surface. Another objective is providing an apparatus capable of treating a variety of medical and dermatological conditions.

The foregoing objectives are attained by the apparatus and method of the present invention.

The disclosures of each of the publications mentioned in this section and in other sections of the specification, are hereby incorporated by reference, each in its entirety.

SUMMARY OF THE INVENTION

The present invention seeks to provide a system for providing a predetermined therapeutic dose of electromagnetic energy of optimal spectrum and optimal pulse duration to a target volume at a predetermined depth beneath the tissue surface, while reducing the thermal exposure of overlying and surrounding tissues. The system preferably comprises a controllable radiation source for generating a radiation beam, and a controllable treatment head. The electromagnetic energy preferably comprises a narrow band light source or a monochromatic light source such as a laser. The treatment head preferably comprises at least one controllable beam conversion system, which is generally reflective in operation.

The tissue is preferably the skin of a subject to be treated, or another body organ having an accessible surface.

In general, the beam conversion system receives the input radiation beam, of predetermined initial fluence, and is operative to spread it out as it reaches the surface of the tissue thereby reducing the average energy fluence on the surface, and at the same time, to recollect the spread-out radiation into beams which cross each other in the target volume at a predetermined depth below the tissue surface, thus exposing the target volume to energy fluence that is substantially higher than the average energy fluence on the surface, without increasing the energy fluence at other skin sites. The beam conversion system thus delivers a therapeutic dose to the target volume and can repeat this action for a plurality of target volumes to cover the entire desired treatment area.

It is to be understood that the beam conversion system of the present invention does not rely on any optical power to converge the spread out radiation components onto the target volume. The beam converter can operate on a pure collimated beam, which can maintain a non-convergent collimated nature as it is spread out, and as the spread out radiation is reassembled. The terms reconverge, reassemble, recombine, recollect or similar, as used and claimed in the application, are not mean to imply optical convergence of a beam, such as is accomplished by an element having optical power, but rather the collection of the spread-out beam components, whether spatially or temporally, such that they meet and cross at the target volume. The input, spread out and reassembled or reconcentrated beam components can be optically converged, diverged or collimated, but the beam converter of the present invention operates in a manner unrelated to these properties.

According to one preferred embodiment, the beam conversion system spreads the radiation beam by reducing the radiation exposure time at the surface while sustaining the radiation exposure time at the target volume. This is achieved by diverting the beam away from the axis of the input beam and then redirecting the beam back inwards towards the input beam axis at a predetermined incident angle to the surface, causing the beam to cross the symmetry axis at the target point, below the surface. The beam is rotated around the axis, thus exposing any given point of the target volume to radiation during the entire energy excitation period, while any given point of the surface is exposed to radiation only during a fraction of the energy excitation period, as the rotating beam passes over it.

According to a second preferred embodiment, the beam conversion system spreads out the input radiation beam by increasing the radiation exposure area at the surface while maintaining the radiation exposure area at the target volume. This is realized by splitting the radiation beam into a plurality of static beams directed away from the input optical axis, and redirecting the plurality of beams inwards, back towards the axis at predetermined incident angles to the surface, such that they reassemble together at a crossing point at a predetermined depth generally at the target volume.

According to another preferred embodiment, a scanning system is added to the beam conversion system, allowing combined functionality of both of the previous embodiments—the time divided beam embodiment and the space divided beam embodiment, as well as improved flexibility in some of the operating parameters of the system.

Additional uses and functions of the present invention include:

1. The simultaneous treatment of multiple targets with different wavelengths and exposure times.
2. Reduction of pain by scanning the treatment area in discrete steps, not adjacent to each other.
3. Cooling of the surface of the skin and epidermal tissue above the targeted dermal region before and/or during the thermal treatment to minimize injury to the surface of the skin while irradiating the skin.
4. Use of multiple sources of energy such as radiofrequency (RF), microwave, ultrasound or other electromagnetic radiation applied simultaneously or sequentially in combination with the light energy.
5. A visible aiming beam that creates a marking spot on the surface of the skin under which the target point is located.
6. A sensing system for determining the speed of rotation of the beam conversion system and for determining the location of the light beam impinging on the surface.
7. Manual repositioning of the beam conversion system to new treatment location.
8. A plurality of treatment heads, arranged in a two-dimensional matrix for simultaneous or sequential operation.
9. A mechanical, two-dimensional positioning system for scanning the treatment area.
10. An optical tracking system for tracking and controlling the location of the target zones in the treatment area
11. A transparent element applied between the treatment head and the surface for improved light coupling into the tissue.
12. An imaging system for assisting in locating the target.

The method and apparatus of the present invention broadly can be used for treating a variety of medical and dermatological conditions such as wrinkles, sagging and folding skin, an excess of unwanted hair, vascular conditions, sub-surface ablation and many other conditions that require thermal treatment.

The method comprises providing an input beam of radiation preferably having a wavelength between 0.3 and 11 microns, providing at least one controllable beam conversion system for spreading out the beam of radiation such that it impinges on the surface of the tissue overlying the target with a larger area than the input beam, thereby reducing the average energy fluence on the surface. The method further comprises reassembling the spread-out beam or beams so that they cross at least one target volume, at a predetermined depth below the tissue surface, thus exposing the target volume to energy fluence substantially higher than the average energy fluence on the surface. In one embodiment the resulting fluence at the target is normally no higher than the fluence of the initially provided beam of radiation. In another embodiment fluence at the target is higher than of the initially provided beam of radiation as might be required by some applications.

The method further comprises repeating this action for a plurality of target volumes consequently or simultaneously, by manually or mechanically repositioning the reflective beam conversion system to cover the desired treatment area. The method further comprises tracking and controlling the location of the target zones in the treatment area. Additionally, the method comprises consequently or simultaneously treating multiple vertically separated target volumes with different wavelengths and exposure times. Furthermore, the method comprises applying gel to the skin surface. The method further comprises utilizing an imaging system for assisting in locating the target.

The invention offers numerous advantages over existing medical and dermatologic procedures and devices.

The non-target tissue layers overlying the target tissue remain intact, thereby avoiding undesirable side effects which may arise when using prior art techniques.

Furthermore, the invention allows the delivery of significantly higher energy fluence to the target than when using prior art methods, which can induce more effective treatment, while still preserving the safety of the procedure. Moreover, delivering higher energy to the target tissue can achieve the desired thermal effect while requiring much less chromophore in the target tissue. Consequently, the selection of radiation wavelength is less restricted by the target chromophore, therefore wavelengths capable of deeper tissue penetration can be utilized thus allowing treatment of deeper targets.

Additionally, because the invention does not require focusing the energy under the surface, the maximum power density at the target is more controllable, resulting in a significantly safer procedure. In addition, the invention does not require refractive optical elements which may have a low numerical aperture and consequent increased danger of damage to the epidermis. Moreover, the invention permits considerably more effective avoidance of overheating of the overlying tissue, either on the surface or even under the surface in close proximity to the target.

Still another advantage is the ability to produce target volumes of desired shape, size, energy distribution and depth under the surface. Yet another advantage of the invention is the ability to simultaneously treat multiple, separate targets at different depths using different wavelengths and different pulse durations.

The invention allows treatment of a variety of medical and dermatological conditions with a single piece of apparatus, while separately optimizing the treatment parameters for each application.

There is thus provided in accordance with a preferred embodiment of the present invention, apparatus for delivering radiation beneath a tissue surface, comprising:
(i) a radiation source for inputting a beam of the radiation of predetermined energy fluence, and
(ii) a beam converter having a symmetry axis, the beam converter adapted to direct the input radiation in a plurality of directions spaced around the symmetry axis and inclined angularly to the symmetry axis, towards at least one target volume disposed on the symmetry axis beneath the surface, wherein
the radiation has an energy fluence at the surface which is lower on the axis than the maximum energy fluence of the radiation on the surface,
the energy fluence of the radiation at the surface is lower than the predetermined energy fluence of the input beam, and
the energy fluence of the radiation at the at least one target volume is higher than the energy fluence of the radiation at the surface.

In accordance with yet another preferred embodiment of the present invention, there is provided apparatus as described in the previous paragraph, and wherein the beam converter comprises a rotator having a rotation axis collinear with the symmetry axis for rotating the input radiation around the symmetry axis, such that the radiation is spread out in a rotational path on the surface. Alternatively and preferably, the beam converter further comprises at least one reflective element for directing the radiation through the surface radially inwards towards the symmetry axis and the target volume. The radiation preferably has a spectral band between 300 nm and 11000 nm.

There is further provided in accordance with yet another preferred embodiment of the present invention apparatus as described above, and wherein the energy fluence of the directed input radiation may be less than or equal to the predetermined energy fluence. Additionally, the radiation at the target volume may preferably have an energy fluence less than or equal to the predetermined energy fluence. Furthermore, in any of the above described embodiments, the rotated radiation may preferably be in a collimated form. Moreover, the distance of the target volume beneath the surface may preferably be adjustable.

In accordance with still another preferred embodiment of the present invention, there is also provided the above mentioned apparatus for delivering radiation beneath a tissue surface, but wherein the beam converter comprises a reflective beam divider for spreading the input radiation in the plurality of directions, and a reflective beam collector for redirecting the spread out radiation towards the target volume. The radiation preferably has a spectral band between 300 nm and 11000 nm, and the energy fluence of the redirected radiation is preferably less than or equal to the predetermined energy fluence.

In any of the above-described apparatus, the at least one target volume may preferably be at least two target volumes, and the radiation is delivered to the at least two target volumes substantially simultaneously. In such preferred embodiments of the apparatus of this invention, the radiation preferably comprises at least first and second spectral bands, and the radiation of the at least first spectral band is delivered to one of the at least two target volumes, and the radiation of the at least second spectral band is delivered to a second one of the at least two target volumes.

There is also provided in accordance with yet another preferred embodiment of the present invention, apparatus for delivering radiation beneath a tissue surface, comprising:
(i) a radiation source for inputting a beam of the radiation, and
(ii) a beam converter having a symmetry axis, the beam converter adapted to direct the radiation in a plurality of directions spaced around the symmetry axis such that the majority of the radiation crosses the surface remotely from the symmetry axis, and inclined angularly towards the symmetry axis. The beam converter may preferably comprise a rotator having a rotation axis collinear with the symmetry axis, for rotating the input radiation around the symmetry axis, such that the radiation is spread out in a rotational path on the surface. Alternatively and preferably, the beam converter may comprise a reflective beam divider for spreading out the input radiation in the plurality of directions, and a reflective beam collector for redirecting the spread out radiation towards the symmetry axis, onto a target volume.

There is further provided in accordance with still another preferred embodiment of the present invention, a method for delivering radiation beneath a tissue surface, comprising the steps of:
(i) providing a radiation source for inputting a beam of the radiation of predetermined energy fluence, and
(ii) converting the input beam into radiation directed in a plurality of directions spaced around a symmetry axis and inclined angularly to the symmetry axis, towards at least one target volume disposed on the symmetry axis beneath the surface, such that:
  the radiation has an energy fluence at the surface which is lower on the axis than the maximum energy fluence of the radiation at the surface,
  the energy fluence of the radiation at the surface is lower than the predetermined energy fluence of the input beam, and
  the energy fluence of the radiation at the at least one target volume is higher than the energy fluence of the radiation at the surface.

In accordance with yet another preferred embodiment of the present invention, there is provided a method as described in the previous paragraph, and further comprising the step of rotating the input radiation around the symmetry axis, such that the radiation is spread out in a rotational path on the surface. This method, according to another preferred embodiment of the present invention, can also comprise the step of providing at least one reflective element for directing the radiation through the surface radially inwards towards the symmetry axis and the target volume. The radiation preferably has a spectral band between 300 nm and 11000 nm. Additionally and preferably, the energy fluence of the directed input radiation may be less than or equal to the predetermined energy fluence. Furthermore, the radiation at the target volume may preferably have an energy fluence which is less than or equal to the predetermined energy fluence.

In accordance with further preferred embodiments of the present invention, in any of the above described methods, the rotated radiation may be in a generally collimated form. Furthermore, the distance of the target volume beneath the surface may preferably be adjustable.

The above-described method for delivering radiation beneath a tissue surface may also comprise the step of providing a reflective beam divider for spreading the input radiation in the plurality of directions, and a reflective beam collector for redirecting the spread out radiation towards the target volume. In such a case, the energy fluence of the directed input radiation may preferably be less than or equal to the predetermined energy fluence, and the radiation may preferably have a spectral band between 300 nm and 11000 nm.

In any of the above-described methods, the at least one target volume may preferably be at least two target volumes, and the radiation is delivered to the at least two target volumes substantially simultaneously. In such preferred embodiments of the methods of this invention, the radiation preferably comprises at least first and second spectral bands, and the radiation of the at least first spectral band is delivered to one of the at least two target volumes, and the radiation of the at least second spectral band is delivered to a second one of the at least two target volumes.

BRIEF DESCRIPTION OF DRAWINGS

The foregoing and other objects, features and advantages of the invention will become apparent from the following more particular description of preferred embodiments of the invention, as illustrated in the accompanying drawings. The drawings are not necessarily to scale, emphasis instead being placed on illustrating the principles of the present invention.

DETAILED DESCRIPTION OF PREFERRED EMBODIMENTS

Figure 1A:
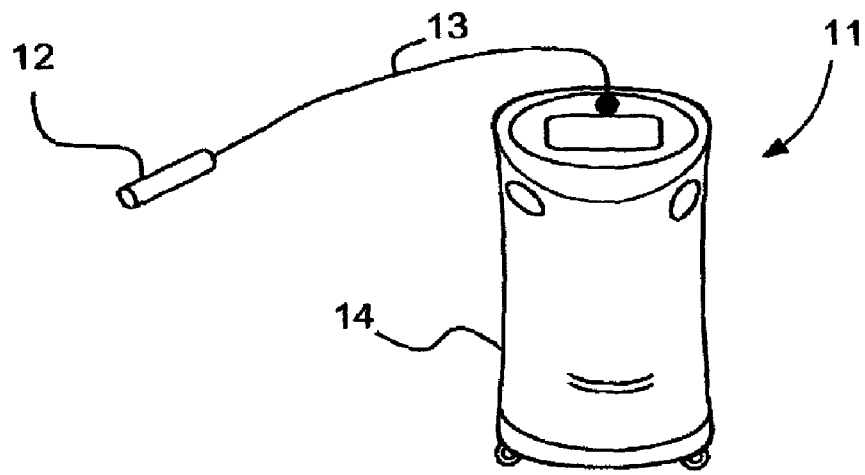
FIG. 1A is a general view the apparatus, including the radiation source a delivery system and the treatment head for practicing the invention.
Figure 1B:
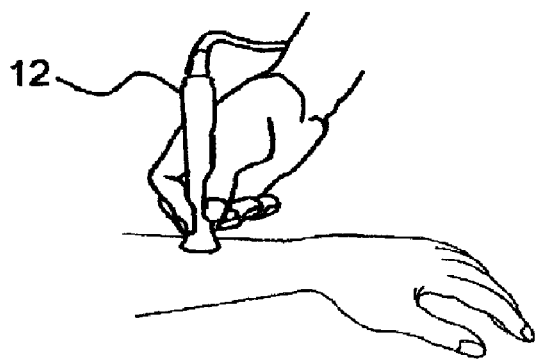
FIG. 1B exemplifies an application of the treatment head on patient's skin.
Figure 1C:
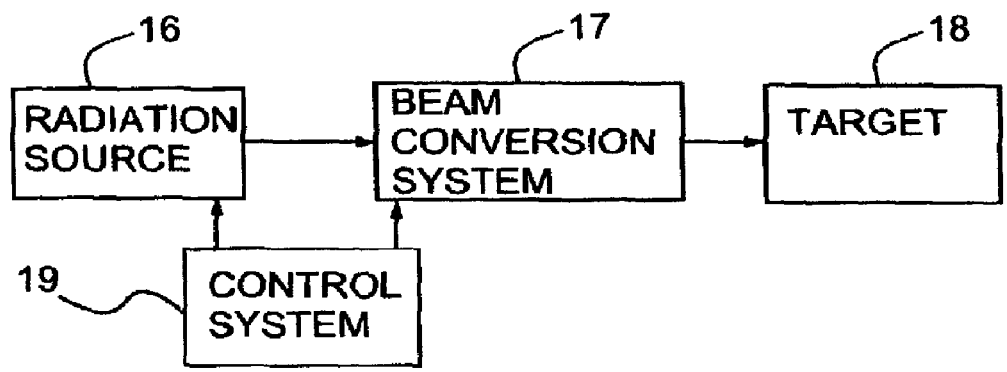
FIG. 1C shows a simplified schematic block diagram of the apparatus.

Reference is now made to FIGS. 1A to 1C, which are schematic illustrations of preferred embodiments of an apparatus 11 for practicing the present invention. In FIG. 1A is shown the apparatus 11 including a controllable radiation unit 14, a delivery system 13 and a treatment head 12. A radiation beam, preferably generated by the radiation unit 14 is directed to a target region via the delivery system 13 and the treatment head 12.

The radiation beam preferably comprises chromatic or monochromatic light such as laser emission. Preferably, the delivery system 13 includes an optical waveguide through which the radiation beam may travel to the treatment head 12. The treatment head 12 includes at least one beam conversion system (not shown in FIG. 1A) that receives the radiation beam, transforms the beam and directs a transformed beam to a treatment area. In one embodiment the treatment area is the subject's skin while the treatment head 12 is a handpiece held by the operator as illustrated in FIG. 1B.

FIG. 1C illustrates a schematic block diagram of a preferred embodiment of the apparatus. The apparatus preferably includes a radiation source 16 for producing the radiation beam, a controllable beam converter or beam conversion system 17 at least one of which is preferably included in the treatment head 12 of FIGS. 1A and 1B, to direct the radiation beam to the target 18, and a control system 19 that is preferably included in radiation unit 14 of FIG. 1A for controlling the radiation source and the beam conversion system. In another embodiment of present invention, the control system 19 is included in the treatment head 12. In yet another embodiment the radiation source 16 is included in the treatment head 12.

The radiation source 16 can preferably be a laser source, which may generate a beam of pulsed or gated CW laser radiation of at least one wavelength. In another embodiment, the radiation source 16 generates a laser beam with a plurality of wavelengths. In another embodiment, the radiation source 16 generates incoherent radiation.

Figure 2A:
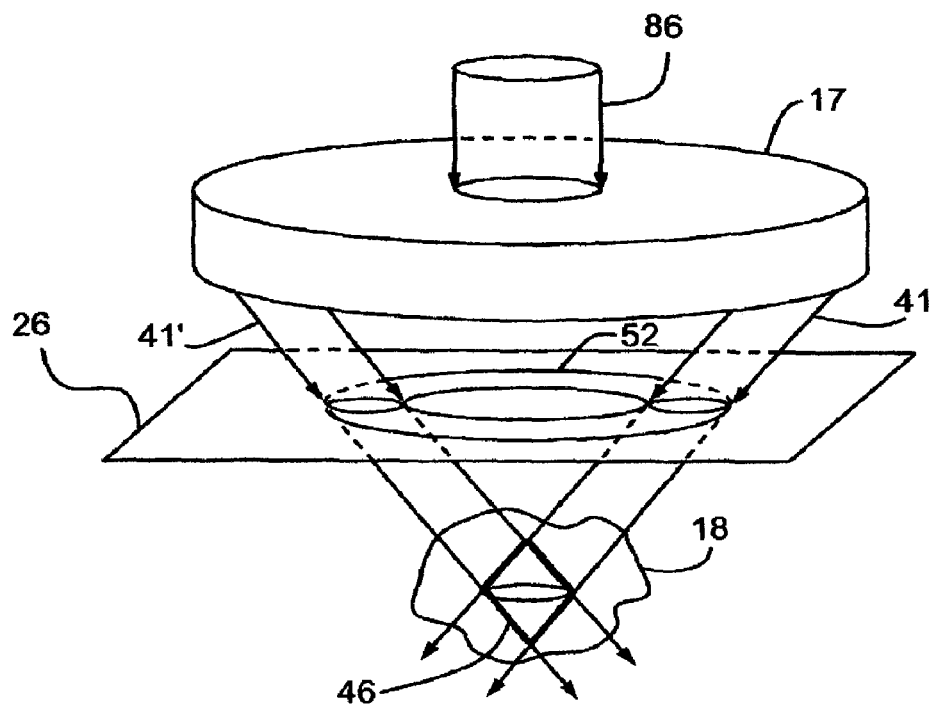
FIG. 2A shows a conceptual illustration of the beam conversion system incorporating the principles of the invention.

Reference is now made to FIG. 2A, which illustrates an applied input radiation beam 86, of a predetermined diameter and a predetermined initial fluence F1, entering the beam conversion system 17. The beam conversion system 17 spreads out the radiation beam 86 into a number of beams, schematically represented in FIG. 2A by two beams 41 and 41', though it is to be understood that the number of beams will preferably be many more, or even a continuum of beams fanned out around the circumference. The beam conversion system 17 then redirects the beams 41 and 41' inwardly towards the surface 26 of the tissue, thus producing, on the surface 26, a spot in a shape of a disk 52, or segments of a disc, having a total area which is larger than the cross section area of the input beam 86. Therefore, the energy fluence F2 on the surface 26 is lower than the input beam fluence F1.

The beams 41 and 41' are directed to cross each other at a predetermined depth below the tissue surface 26, to produce an overlap volume defined as target volume 46. The combined fluence F3 at the target volume 46 is higher than the average energy fluence F2 on the surface. The fluence F3 can be made less than, equal to, or greater than the input fluence F1, according to whether the beam conversion system applies any convergence or divergence to the treatment beams 41 and 41', and whether the input beam 86 itself is a collimated beam or a divergent or convergent beam.

The beam conversion system 17 thus delivers a therapeutic dose of radiation to the target volume 46 while delivering a reduced dose of radiation to overlying and surrounding tissues. The beam conversion system 17 can be moved around to treat a plurality of target volumes to cover the desired treatment area. For clarity, the term "therapeutic dose" is understood to mean the amount of energy necessary to thermally affect the targeted region to elicit the therapeutic effect required in a specific application.

According to one preferred embodiment, the beam conversion system 17 provides the spread of the input beam 86 by reducing the radiation exposure time of the surface while sustaining the radiation exposure time of the target volume. This is preferably realized by causing the output beam from the beam converter to rotate around the axis of the input beam, thus exposing the target volume during the entire energy excitation period, while exposing the surface to radiation only during a fraction of the energy excitation period. The beam rotation period may preferably be made equal to the energy excitation period, or shorter.

Figure 2B:
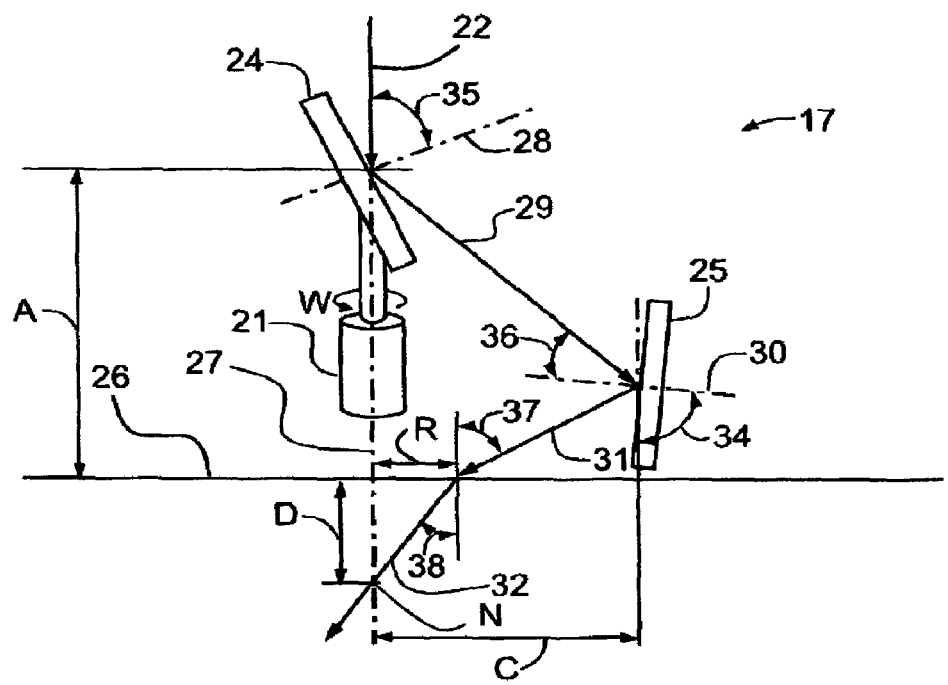
FIG. 2B illustrates one embodiment of the beam conversion system incorporating the principles of the invention.

Reference is now made to FIG. 2B which schematically illustrates one preferred embodiment of the beam conversion system 17 including a pair of mirrors 24, 25 and a rotator 21, controlled by the control system 19 of FIG. 1C. The mirror 24 is rotated about an axis 27 by a rotator 21, such as an electric motor. The point of intersection of the mirror and the rotation axis is a distance A from the surface 26. The mirror is mounted in such position that the normal 28 to the surface of the mirror 24 lies at an angle 35 to the rotation axis 27. The rotation axis 27 is preferably perpendicular to the surface 26. The second mirror 25, is also connected to the rotation axis turned by the rotator 21, and is arranged at a distance C from the axis 27 in a position facing the mirror 24, such that the normal 30 to the surface of the mirror 25 lies at an angle 34 to the normal to surface 26 (and the axis 27). Preferably, the normal 30 lies in the plane defined by the rotation axis 27 and the normal 28.

During an excitation mode, a preferably collimated beam, a center of which is defined by vector 22, propagates from the radiation source 16 of FIG. 1C, in a direction generally aligned with the rotation axis 27, impinging on the mirror 24 at an angle 35 to the normal 28 to produce a reflected beam, a center of which is defined by a vector 29, which impinges on the mirror 25 at an angle 36 to the normal 30 to produce a reflected beam, a center of which is defined by a vector 31. The mutual geometrical arrangement of the mirrors is such that the reflected beam impinges the surface 26 at an angle of incidence and is directed towards the target area below the surface, and generally on the axis 27.

As the rotator 21 rotates the mirrors 24 and 25 at an angular velocity W about the symmetry axis 27, the vector 31 traces a circle of radius R on the surface 26 around the symmetry axis 27. In one embodiment a sensor (not shown), connected to the control unit 19, is provided for determining the speed of rotation of the beam conversion system 17 and for determining the location of the light beam impinging on the surface 26.

Angle 37 is the angle of incidence between the vector 31 and the normal to the surface 26. A refracted beam, represented by vector 32, penetrates the tissue with a refraction angle 38.

According to Snell's Law: n1*sin(angle 37)=n2*sin(angle 38), where n1 is the refraction index of the interposing medium, for example air, while n2 is the refraction index of the tissue beneath the surface, for example the cutaneous tissue. The index of refraction of the cutaneous tissue is approximately 1.5. Therefore, the angle 38 is smaller than the angle 37.

As the vector 31 traces a circle having radius R on the surface 26, the vector 32 rotates around the rotation axis 27 and crosses it at a target point N, which is located at the depth of D below the surface 26.

The angles 35, 36, 34 and 37 and the distances A and C are all known by design. The refraction index for a variety of materials is known in the art. Therefore, the distance D can be calculated using simple trigonometry laws.

Assuming for simplicity that angle 34 is 90 degrees, the distance D can be calculated as follows:

$$D=(2*C-A*\tan(\text{angle}37))/(\tan(\text{angle}38))$$

The angle 38 is equal to $\arcsin((n1/n2)*\sin(\text{angle}37))$. Therefore:

$$D=(2*C-A*\tan(\text{angle}37))/((\tan(\arcsin((n1/n2)*\sin(\text{angle}37))))$$

According to further preferred embodiments of the present invention, the radiation source 16 of FIG. 1C may be incorporated into the beam conversion system 17. Reference is now made to FIG. 3F schematically illustrating a beam conversion system 17 according to such a preferred embodiment of the present invention, which includes a radiation source 20, such as a laser diode or the output end of the optical delivery system 13 of FIG. 1A, mounted on the rotator 21 instead of mirror 24 of FIG. 2B. During an excitation mode, a beam propagates from the radiation source 20, impinging on the mirror 25F. The rotator 21 rotates the radiation source 20 and the mirror 25 about the symmetry axis 27 to trace a generally circular path on the surface 26 around the symmetry axis 27.

Figure 3A:
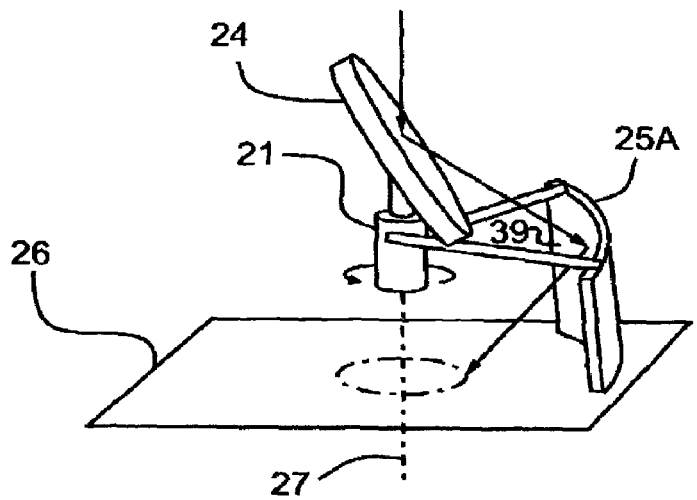
FIG. 3A to 3E illustrate a perspective view of different embodiments of the beam conversion system incorporating the principles of the invention. The different embodiments allow creating target volumes of various shapes.
Figure 3B:
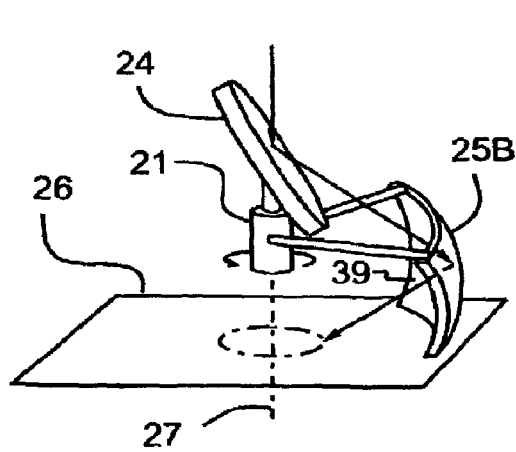
Figure 3C:
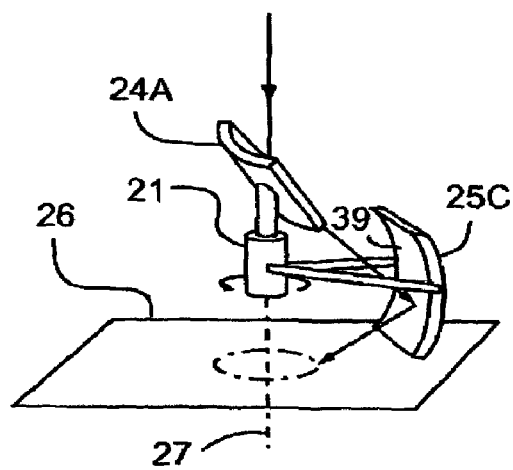
Figure 3D:
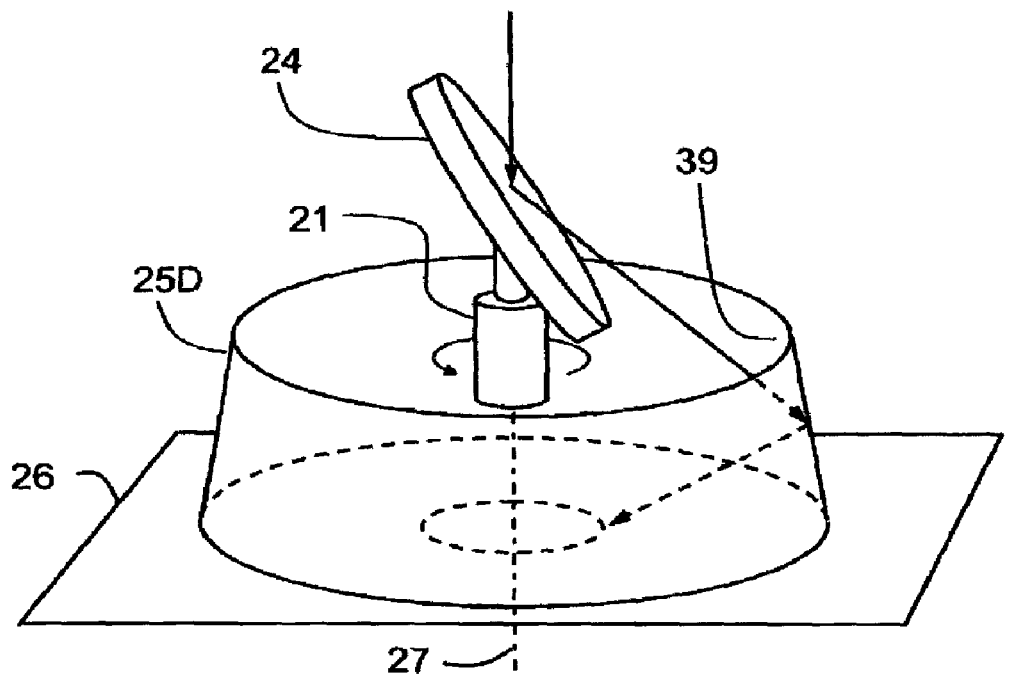
Figure 3E:
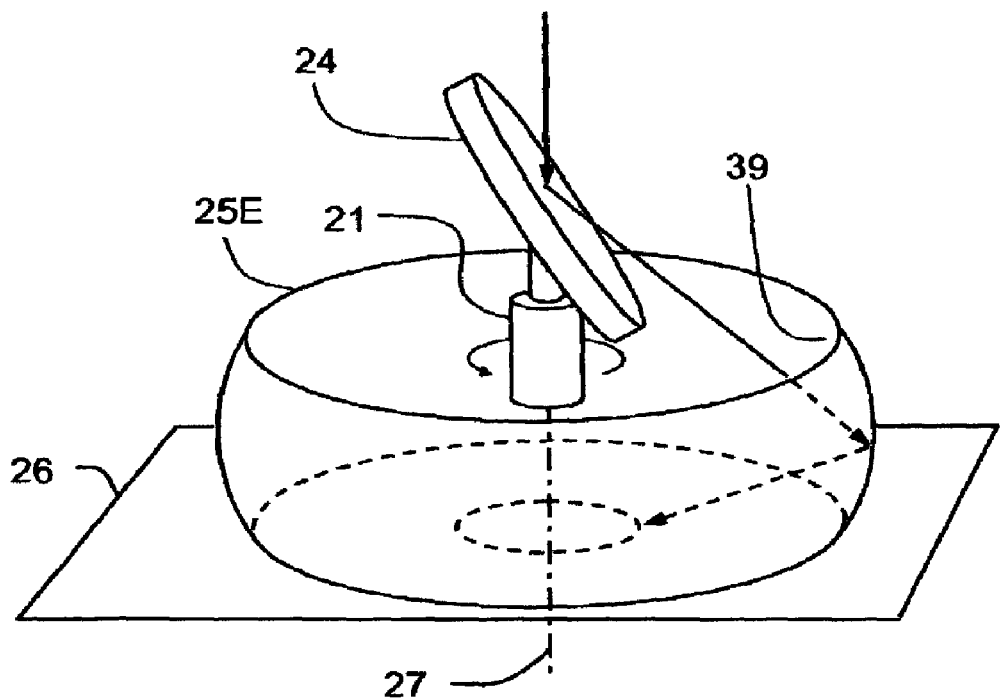
Figure 3F:
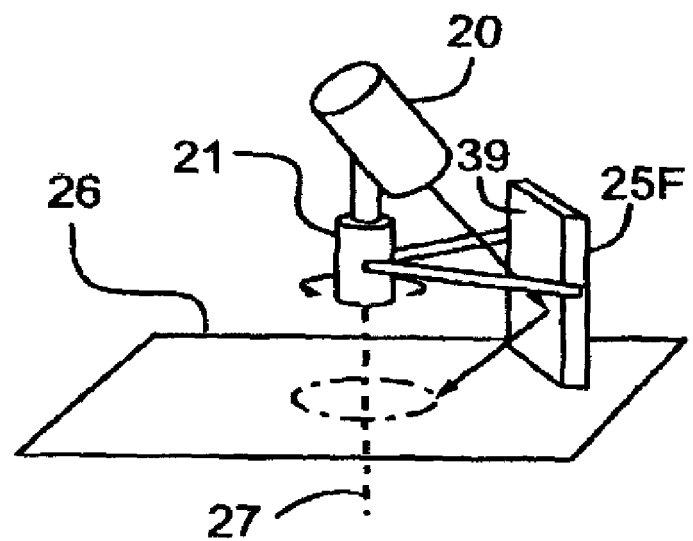
FIG. 3F illustrates another embodiment of the beam conversion system incorporating the principles of the invention in which the radiation source is included in the conversion system.
Figure 3G:
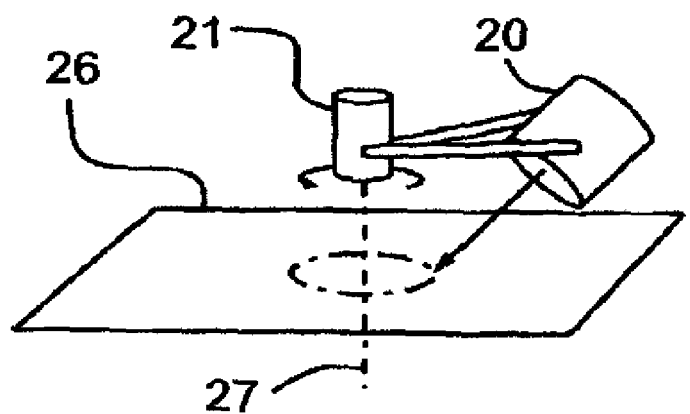
FIG. 3G illustrates another embodiment of the beam conversion system in which the radiation source is used without reflecting elements.

Reference is now made to FIG. 3G illustrating another such preferred embodiment whereby at least one radiation source 20 is connected to the rotator 21 instead of mirror 25 of FIG. 2B. The rotator 21 rotates the radiation source 20 to trace a generally circular path on the surface 26 around the symmetry axis 27.

In any of the embodiments of FIGS. 3F and 3G, the source 20 could preferably be the output end of a fiber optical beam delivery system.

Figure 4A:
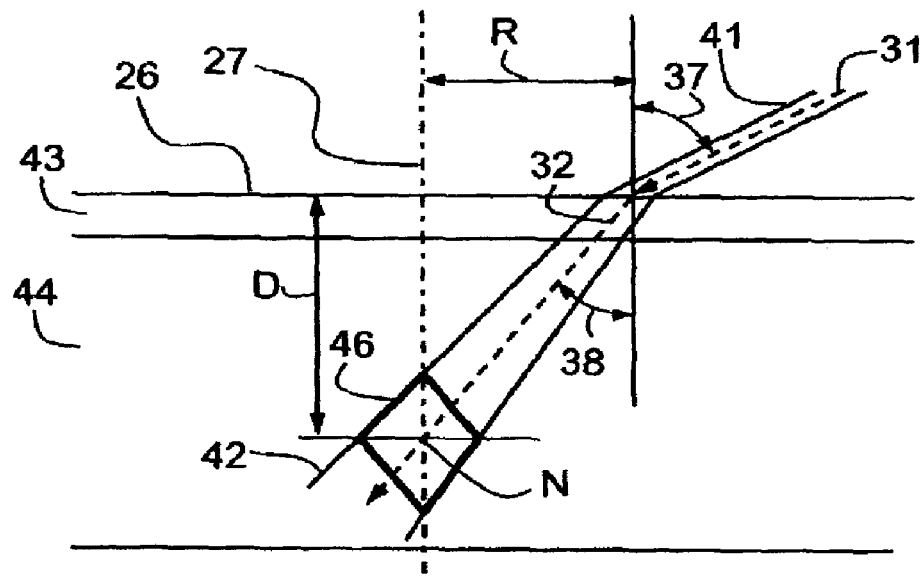
FIG. 4A illustrates an interaction between the laser beam and the tissue according to the principles of the invention.

Reference is now made to FIG. 4A which illustrates penetration of an incidence laser beam 41 into the surface 26. In a preferred embodiment the surface 26 is surface of the skin that includes a layer of epidermis 43 and an underlying dermis 44. The beam 41 having a center represented by the vector 31 traces a circle having radius R on the surface 26. Due to scattering effect, a refracted beam 42, a center of which is represented by vector 32 is divergent. The divergence angle generally depends on tissue optical properties and is inversely related to the wavelength. The center of the beam 42 crosses the axis 27 at target point N located at a depth D below the surface 26. If during the rotation of the beam conversion system 17 of FIG. 1C, the radiation source 16 of FIG. 1C emits energy, the target volume 46 is continuously exposed to radiation. The beam 42 normally has a Gaussian power distribution with a maximum energy at the center of the beam. The target point N receives maximum thermal dose and therefore defines a thermal center of the target volume 46.

The extent of thermal damage to the tissue is directly proportional to power density or irradiance and the exposure time. If the exposure time is shorter than the target's thermal relaxation time (defined as the time required for a target to cool from the temperature achieved immediately after laser irradiation to half that temperature), heat will not be able to diffuse out. This allows the thermal damage to be limited to the target volume 46. The optimal exposure time may vary in different applications.

Figure 4B:
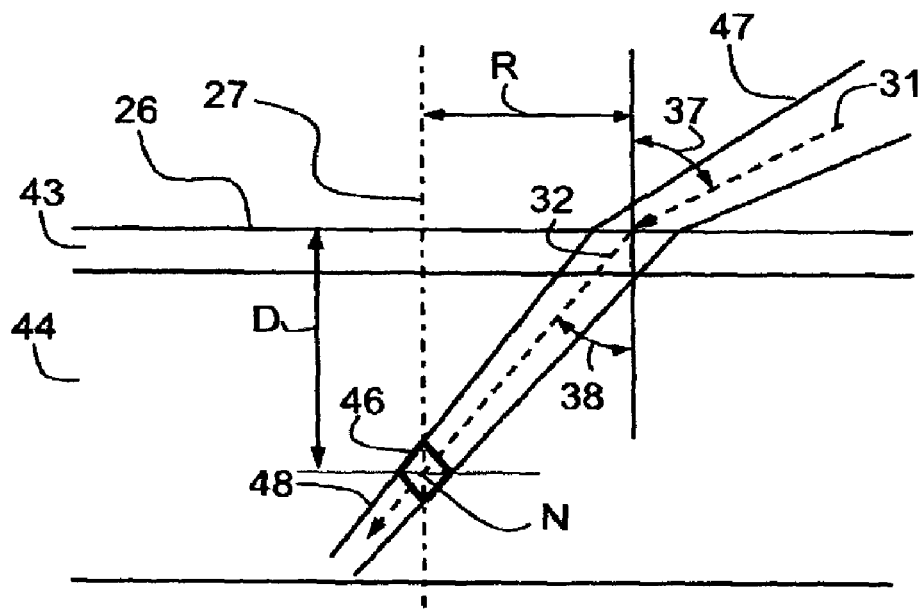
FIG. 4B illustrates another embodiment of the interaction between the laser beam and the tissue according to the principles of the invention.

Referring now to FIG. 4B, in one specific embodiment, to counteract the effects of scattering, the beam 41 of FIG. 4A is made convergent. It must be emphasized that the convergence is normally directed to a region located far beyond the treatment zone. To achieve that, in one embodiment, the radiation beam 86 is made convergent using techniques known in the art, prior to entering the beam conversion system 17. Such convergence can be symmetrical or in one specific dimension as could be achieved using cylindrical lenses known in the art.

In another embodiment the convergence of beam 41 can be achieved by modifying the shapes of the reflecting surfaces of the mirror 24 and the mirror 25 of FIG. 2B. This embodiment allows making the beam convergent in two planes separately, thus manipulating the cross sectional geometry of the beam 41, thereby controlling the cross-sectional power distribution of the beam 41. For example, the cross section of beam 41 can be made elliptical. Such manipulation can assist in producing target volumes 46 of different shapes.

Reference is now made to FIG. 3A which schematically illustrates a perspective view of one embodiment in which the convergence is made in the plane parallel to surface 26. In this embodiment, the mirror 25 consists of a cylindrical reflector 25A with an inner reflecting surface 39. The reflector 25A rotates with the mirror 24.

In another preferred embodiment the inner reflecting surface 39 of the reflector 25B is a concave mirror as illustrated in the schematic illustration of FIG. 3B. The configuration shown in FIG. 3A provides convergence of the beam in a plane generally parallel to the tissue surface 26, while the configuration shown in FIG. 3B additionally provides convergence of the beam in a second plane, generally perpendicular to the tissue surface 26. A similar effect can be achieved by modifying the shape of the reflecting surface of the mirror 24.

FIG. 3C illustrates a perspective view of another preferred embodiment in which a cylindrical reflector 24A produces convergence in a plane parallel to surface 26, while the cylindrical reflector 25C produces convergence in a plane perpendicular to surface 26. Therefore, the convergence can be produced independently both in the plane parallel to the surface 26 and in the plane perpendicular to the surface 26.

Reference is now made to FIG. 3D which schematically illustrates a perspective view of one preferred embodiment in which the convergence is made in a plane parallel to the tissue surface 26. In this embodiment, the mirror 25 of FIG. 2B consists of a right circular conical frustrum reflector 25D with an inner reflecting surface 39. The symmetry axis of the reflector 25D is aligned with the symmetry axis 27. In one embodiment, the reflector 25D rotates with the mirror 24, while in an alternative embodiment the reflector 25D is static.

Reference is now made to FIG. 3E which schematically illustrates a perspective view of another preferred embodiment in which the inner reflecting surface 39 of the conical frustrum reflector 25E is a concave mirror having its curvature in the same plane as that of mirror 25B of FIG. 3B. The configuration shown in FIG. 3D provides convergence of the beam in plane generally parallel to the tissue surface 26, while the configuration shown in FIG. 3E additionally provides convergence of the beam in a second plane, generally perpendicular to the tissue surface 26. In both embodiments shown in FIGS. 3D and 3E, the convergence of the beam in a plane generally parallel to the tissue surface 26 produces a focal point, located outside the tissue. However, the redivergence of this focused beam before it impinges the tissue surface ensures that the desired spreading effect is maintained.

In a further preferred embodiment, the beam 41 is generally collimated, while in another embodiment it is substituted by a convergent beam 47 as illustrated in FIG. 4B. The refracted beam 48 is convergent to compensate for the scattering effect of the tissue, or in another embodiment the convergence can be more severe, resulting in a smaller and more intense target volume 46. The convergence of beam can be achieved by any of the preferred configurations described above.

The shape, size, power intensity distribution and depth below surface 26 of the target volume 46 depends on the diameter of the laser beam, a cross section power distribution of the beam, the refraction angle 38 and other geometric parameters as shown above. Some of those parameters can be dynamically manipulated using the principles of present invention. Moreover, those parameters can be altered during duration of a single energy pulse or during a single rotation cycle of the rotating elements of the beam conversion system 17. For example, the target point N can be altered, thus altering the depth D of target volume 46 during a single rotation cycle. This can be accomplished if, for example, instead of the circular conical frustrum 25D in FIG. 3D a conical frustrum with elliptical cross section is applied. In such a case, the target point N will sweep along the axis 27, between two vertical points. The distance between those points is determined by the ratio between the semi-major and semi-minor axis of the ellipse. In another example, the target volume 46 can be made wider and shorter by making the beam 41 convergent in plan parallel to surface 26. This can be useful for applications requiring targeting relatively shallow layers of the tissue.

Figure 6A:
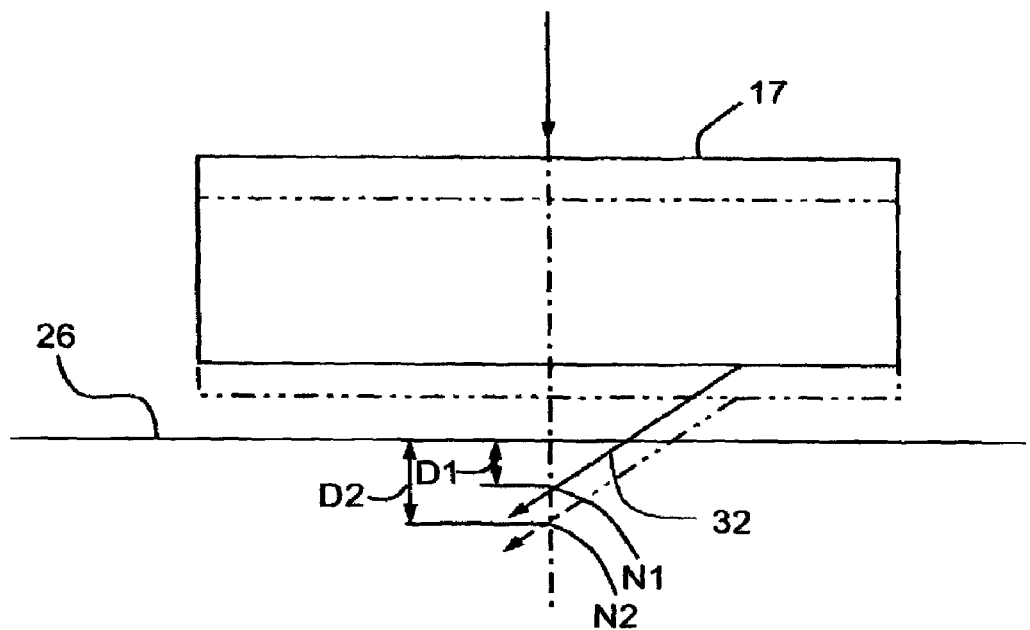
FIG. 6A illustrates the beam conversion system in two different distances from the surface.

To control the depth below the surface 26 of the target volume 46, the distance D and the radius R can be dynamically adjusted as illustrated in FIG. 6A. When the beam conversion system 17 is positioned at a first distance from the surface 26, the target point N1 is at a depth D1. When the beam conversion system 17 is positioned at an alternate distance from the surface 26, the target point N2 moves to a depth D2. The beam conversion system 17 is repositioned vertically using any linear positioning device known in the art, controlled by the control unit 19.

In another embodiment of present invention, with reference to FIG. 2B and FIG. 4A, the radius R and the distance D are adjusted by changing one or more of angles 34, 35 or the distance between the mirrors 24 and 25 or the distance between each of the mirrors 24 and 25, and the surface 26.

Figure 6B:
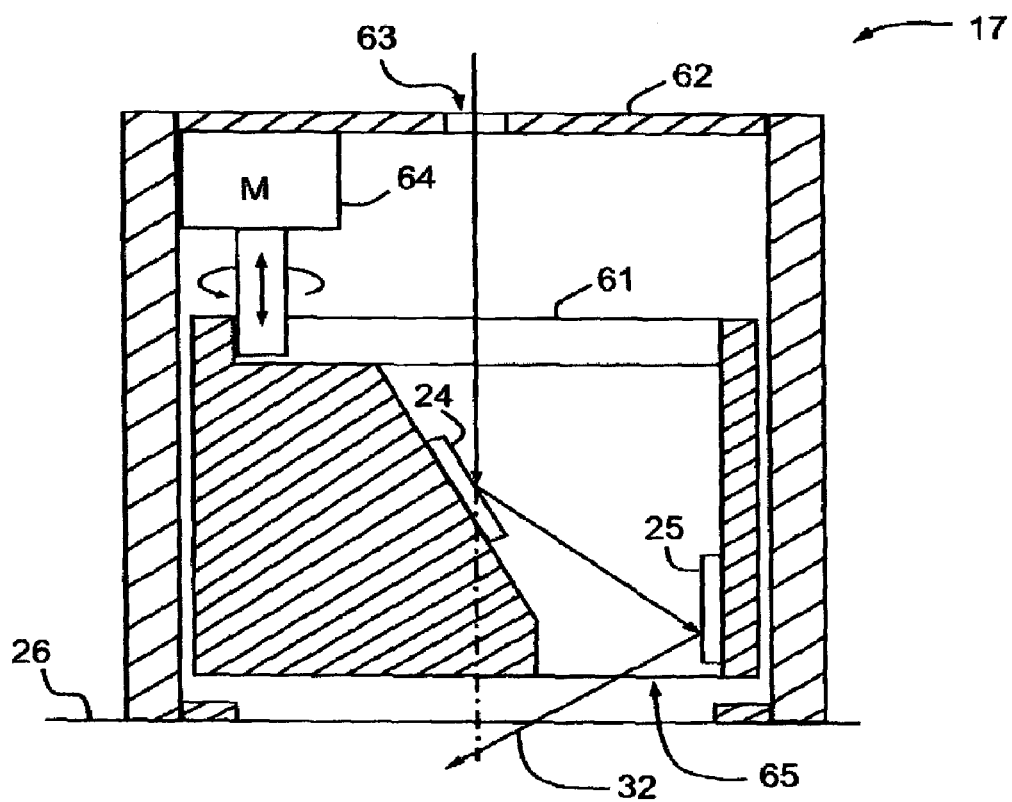
FIG. 6B shows a cross section of the optical head constructed according to the principles of the present invention.

Reference is now made to FIG. 6B which schematically illustrates one embodiment of the beam conversion system 17, constructed in accordance with the principles of the present invention. The beam conversion system 17 includes a cylindrical structure 61 containing both mirrors 24 and 25. The mirrors may be separate elements, available from Laser Beam Products (Cambridge UK), attached to the structure 61 or they may be polished surfaces of the structure 61. A rotation means in this case is a controllable dual motion activator 64 that has both rotary and linear motion, such as is supplied by Haydon Switch & Instrument, of Waterbury, Conn. The beam conversion system 17 also includes an external cylindrical enclosure 62 to which the activator 64 is mechanically attached. The enclosure 62 also includes an opening 63 for the laser beam to enter the beam conversion system and an opening 65 through which a redirected beam, represented by the vector 32, exits the beam conversion system. The rotation means provides both the rotation of the structure 61 and its vertical movement, controllable by control system 19 of FIG. 1C.

As explained above, the location of the target point N along the axis 27 as specified by the distance D is dynamically adjustable. Therefore, by controlling the amount of transmitted energy and the location of the target point N, a target zone of a desired form and size can be created.

Figure 5A:
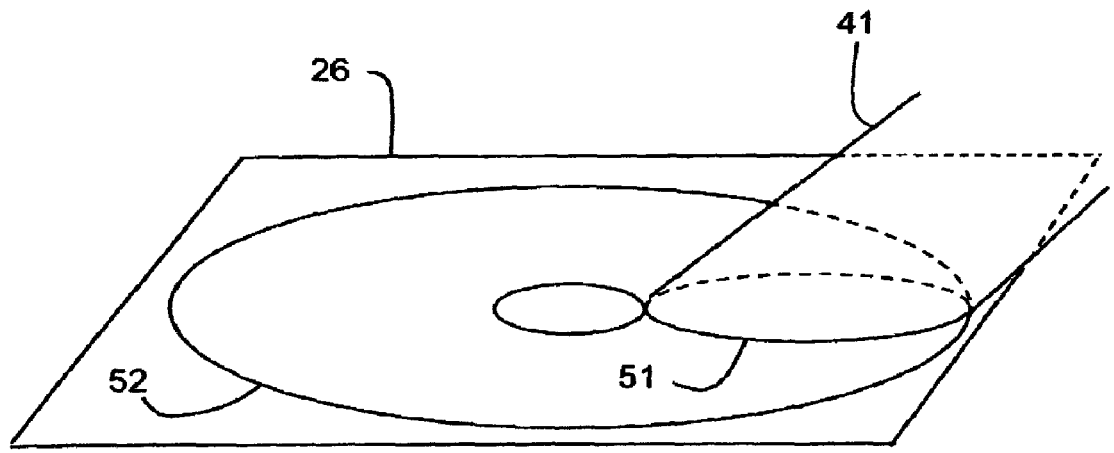
FIG. 5A shows a perspective view of the light beam projected on the surface in accordance with the principals of the present invention.

Reference is now made to FIG. 5A which schematically illustrates a perspective view of an elliptical spot 51 produced by the projection of the beam 41 on the surface 26. As the beam conversion system rotates, it projects the elliptical spot 51 on the surface 26 in a form of a disk 52. The area of the disk 52 is significantly larger than the area of the elliptical spot 51. An average exposure time of any single point on the disk 52 during one rotation cycle is therefore significantly smaller than the period of the cycle. The thermal effect of light energy on the surface 26 depends on the energy fluence or power density of the light beam multiplied by the exposure time to the light beam. For any given power density, the reduced exposure time results in significantly less fluence and consequently less damage to the surface 26 of the tissue. If the tissue treated is the skin, less damage is caused to the superficial layers of the skin such as the epidermis and papillary layer of the dermis.

The following numerical example can be used to illustrate the reduced exposure to the surface of the tissue. Referring to FIG. 4A, and assuming that the beam 41 is delivered in pulses of duration equal to one rotation period of the beam 41, that the angle 37 is 45 degrees, and the refraction index of the skin is 1.44, the refraction angle 38 is approximately 29.4 degrees. If the diameter of the beam 41 is 0.8 mm and the required penetration depth D is 2 mm, the area of the disk 52 is 6.51 square mm while the area of the ellipse 51 is 0.58 square mm. The ratio between the areas of the ellipse 51 and the disk 52 is proportional to the average exposure time of the surface of the disk 52 during the rotation cycle. It this example, this ratio is 0.089 which means that the average exposure time of the surface of the disk 52 is approximately 8.9 percent of the rotation period. Consequently, the surface average fluence is 8.9 percent of the average fluence of the beam 41 in an idle position.

Instead of generating the beam spreading effect by means of a rotating structure, the beam conversion system 17 can, according to other preferred embodiments of the present invention, provide the spread of the input radiation beam 86 statically by increasing the radiation exposure area at the surface while maintaining the radiation exposure area of the target volume. This is realized by splitting the radiation beam into a plurality of beams, redirecting the plurality of beams at predetermined incident angles inwards towards the surface, and pointing towards the symmetry axis which is generally normal to the surface, such that the plurality of beams are reassembled into the target volume at a predetermined depth.

Figure 7A:
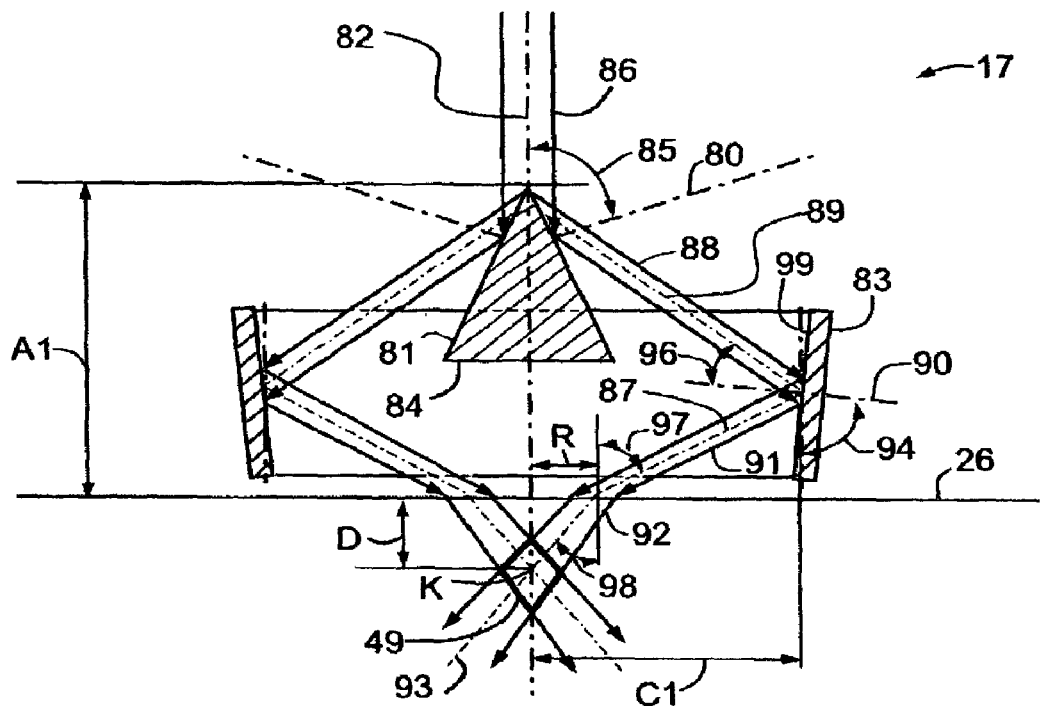
FIG. 7A shows a cross section of another embodiment of the beam conversion system incorporating the principles of the invention.

Reference is now made to FIG. 7A which schematically illustrates a cross section of such a preferred embodiment of the beam conversion system 17 that includes a right angular cone 84 that has a symmetry axis 82, generally normal to the surface 26 and a reflecting surface 81. The angle between the axis 82 and a normal 80 to the surface 81 is an angle 85. The element 84 does not have to be a cone, which reflects a fanned out beam in all directions. It could be a facetted mirror, which reflects a number of discrete radial beams. Either of the reflectors can be in a variety of geometric forms and configurations suitable for both collimated and convergent beams.

The beam conversion system 17 further includes a right circular conical frustrum reflector 83 with an inner reflecting surface 99 and a symmetry axis preferably aligned with the symmetry axis 82. The angle between the normal to the surface 26 and the normal to the reflecting surface 99 is an angle 94.

The distance between the symmetry axis 82 and the reflecting surface 99 is C1. The distance between the top of the cone 84 and the surface 26 is A1.

During an excitation mode, a laser beam 86, a center of which is defined by a vector that is aligned with the symmetry axis 82, propagates from the radiation source 16 of FIG. 1C. The beam 86, impinging on the reflecting surface 81 at an angle 85 to the normal 80, will produce a plurality of reflected beams spreading outwards the symmetry axis 82. These reflected beams are schematically represented by a beam 88, a geometry center of which is defined by a vector 89. The reflected beams represented by the beam 88 impinging on the reflecting surface 99 at an angle 96 to a normal 90 will produce a plurality of reflected beams. The plurality of reflected beams, one of which is schematically illustrated by a beam 91, a center of which is defined by a vector 87, directed inwards the symmetry axis 82. The geometry center of the beam 91 defined by the vector 87 does not necessarily represent the maximum cross sectional energy density of beam 91.

The plurality of beams, one of which is schematically illustrated by the beam 91, a center of which is illustrated by the vector 87 creates a circle of radius R on the surface 26 around the symmetry axis 82. Angle 97 is an angle of incidence between the vector 87 and the normal to the surface 26.

The plurality of beams one of which is schematically illustrated by the beam 91, penetrate the surface 26, to create a plurality of refracted beams, one of which is schematically illustrated by a beam 92, a center of which is defined by a vector 93. An angle between the vector 93 and the normal to the surface 26 is a refraction angle 98. Due to scattering effect, the refracted beam 92 may be moderately divergent.

Similar to the embodiments illustrated in FIG. 2B and described above, the geometric centers of the plurality of beams, one of which schematically illustrated by a beam 92, cross each other at a target volume 49. A geometric center of volume 49 is represented by point K, which is located at the depth of D below the surface 26. The angles 85, 96, 94 and 97 and the distances A1 and C1 are all known by design. The refraction index for variety of materials is known in the art. Therefore, the distance D can be calculated using simple trigonometry laws. In a preferred embodiment of the present invention, the radius R and the distance D can be dynamically adjustable by for example controlling the distance A1 or the distance between the beam conversion system 17 and the surface 26.

Figure 7B:
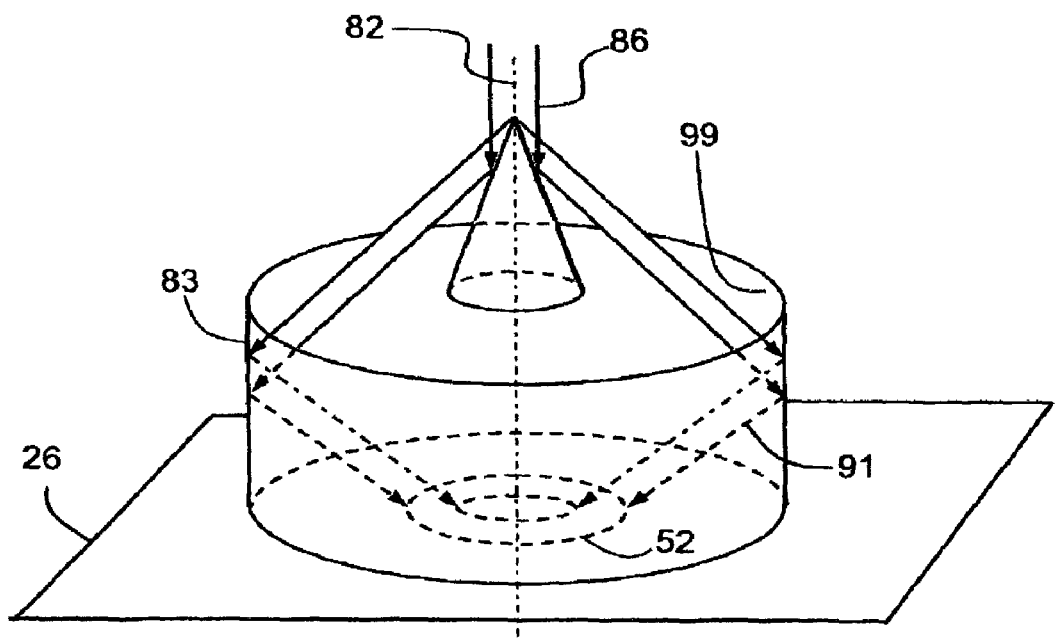
FIG. 7B illustrates a perspective view of another embodiment of the beam conversion system incorporating the principles of the invention.

FIG. 7B exemplifies one such system. FIG. 7B illustrates a perspective view of the beam conversion system 17 of FIG. 7A that illustrates a specific embodiment in which the surface 83 is a cylinder. The angle 94 between the symmetry axis 82 and the reflective surface 99 is 90 degrees.

The shape and the size of the target volume 49 mostly depend on the diameter of the laser beam, the cross section power distribution of the beam, the refraction angle 98 and the scattering effect of the tissue. Due to geometric considerations, the thermal exposure will be symmetrically distributed around the symmetry axis 82. However, in this embodiment, the point K will not necessarily receive maximum thermal dose.

The shape and the size of the target volume 49 as well as the energy distribution are controllable to fit the desired application.

It should be emphasized that in these preferred embodiments, the beam 86 is generally collimated. Moreover, the beam conversion system does not focus the beam 86 at any point, thus the fluence at any point is no higher then the fluence of the beam 86.

According to another preferred embodiment, to counteract the effects of tissue scattering, the beam 91 is made convergent. To achieve this, in one preferred embodiment, the radiation beam 86 is made convergent using techniques known in the art, prior to entering the beam conversion system 17. In another embodiment, beam convergence on the surface 26 can be achieved by modifying the shape of the reflecting surface 81 of the cone 84 and the reflecting surface 99 of the frustrum 83 of FIG. 7A.

For example, similarly to the embodiment illustrated in FIG. 3A the convergence of the beam 91 is made in the plane generally perpendicular to the surface 26 by making the surface 99 of the frustrum 83 of FIG. 7A a concave reflector having reflective surface similar to the reflective surface 39 illustrated in FIG. 3E. Such manipulation can assist in producing a target volume 49 of a desired shape.

In another preferred embodiment, instead of the right angular cone 84, a spherical cap is used. Accordingly, instead of the right circular conical frustrum reflector 83, a second spherical cap with an inner reflecting surface and a symmetry axis preferably aligned with the symmetry axis 82 is used. It should be appreciated that present invention can be practiced using reflectors in a variety of geometric forms and configurations suitable for both collimated and convergent beams.

The shape, size, power intensity distribution and depth below the surface 26 of the target volume 49 is mostly depend on the diameter of the laser beam, the cross section power distribution of the beam, the refraction angle 98 and other geometric parameters as shown above. Some of those parameters can be dynamically manipulated using further embodiments of the present invention. Moreover, some of those parameters can be altered during the duration of a single energy pulse. For example, the distance D of the target point K can be altered thus altering the depth of target volume 49 during a single energy pulse. This can be accomplished, for example, if instead of circular conical frustrum 83 in FIGS. 7A-B, a conical frustrum with elliptical cross section is used. In such a case, the target point K will be sweeping along the axis 82, between two vertical points. The distance between those points is determined by the ratio between the semi-major and semi-minor axis of the ellipse.

To control the depth below surface 26 of the target volume 46, the distance D the radius R can be dynamically adjusted as illustrated in FIG. 6A and as explained hereinabove.

In another embodiment of present invention, with reference to FIG. 7A, the radius R and the distance D are adjustable by changing one or more of angles 85, 94 or the distances C1 and A1.

Referring now to FIG. 7B, the plurality of reflected beams, one of which is schematically illustrated by the beam 91 projecting illumination in the form of the disk 52 on the surface 26. The surface of the disk 52 is significantly larger than the surface of the cross section of the beam 86. Therefore, for any given exposure time, the power density at any specific point on the surface of the disk 52 is significantly lower than the power density of the beam 86. The reduced power density results in significantly less damage to the superficial layers of the tissue. If the tissue treated is the skin, less damage is caused to the superficial layers of the skin such as the epidermis and papillary layer of the dermis.

Figure 8A:
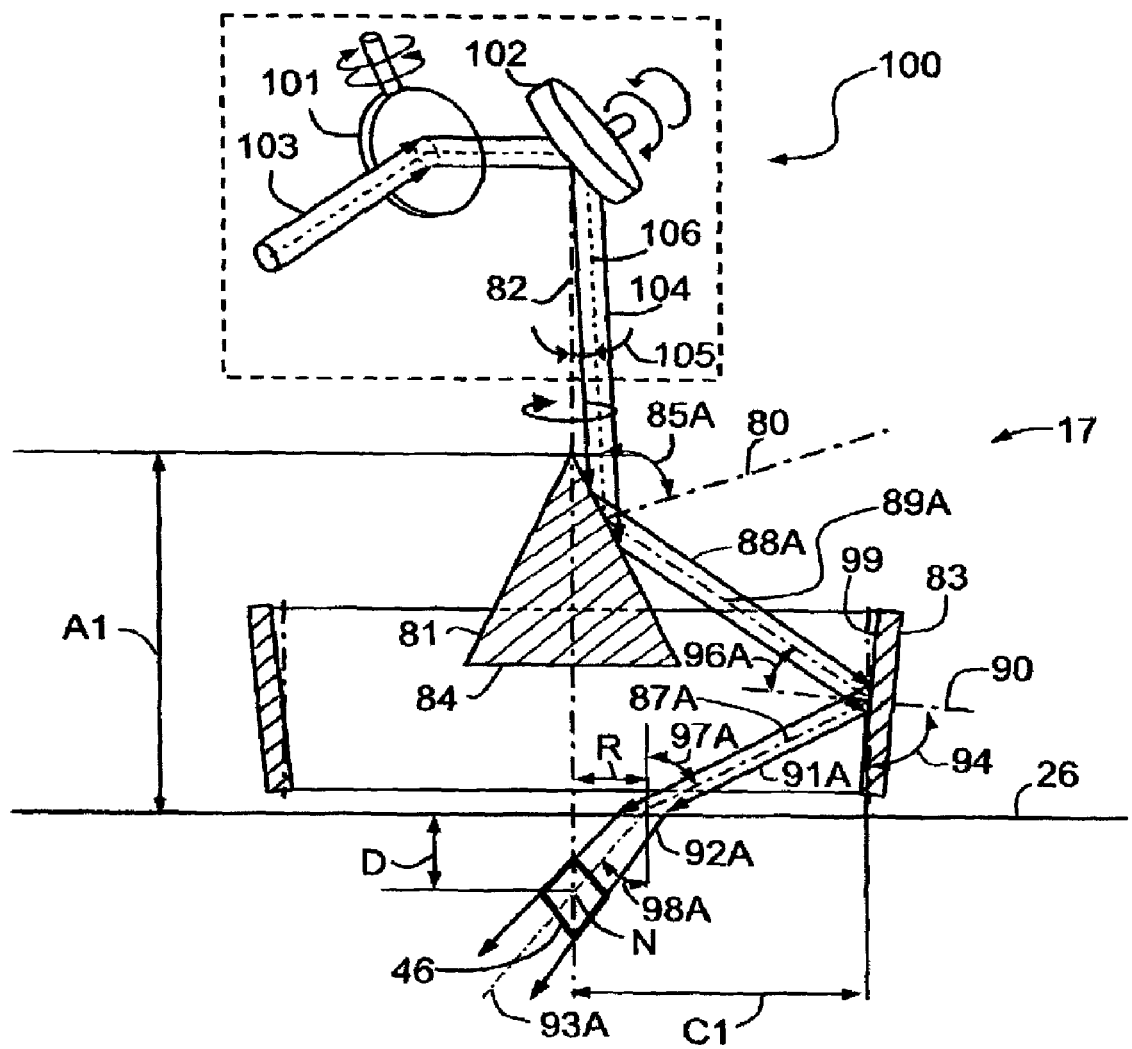
FIG. 8A illustrates a combination of schematic and perspective view of another embodiment beam conversion system incorporating the principles of the invention.

Reference is now made to FIG. 8A, which schematically illustrates another preferred embodiment of the beam conversion system 17. In addition to the beam conversion system 17 described above as illustrated in FIG. 7A which includes a right angular cone 84 and a right circular conical frustrum reflector 83, this embodiment also includes a scanning system 100. The scanning system 100 directs the beam 103, propagating from radiation source 16 of FIG. 1C. in a circular, spiral or any desired pattern around the axis 82. This can preferably be accomplished using techniques known in the art, for example applying a galvanometric scanner with mirrors 101 and 102 operated at 90 degrees out of phase. Suitable galvanometers can be supplied by GSI Lumonics, of Moorpark, Calif.

During the excitation mode, the laser beam 104 propagates from the scanning system 100 with an angle 105 between the symmetry axis 82 and a center of the beam 105, which is defined by vector 106. The beam 104, after being reflected from the reflecting surface 81 at the angle 85A to the normal 80, is represented by a beam 88A, a center of which is defined by a vector 89A, which thereafter is reflected from the reflecting surface 99A at an angle 96A to the normal 90 to surface 99, schematically illustrated by a beam 91A, a center of which is defined by a vector 87A.

As will be shown in the following description, this embodiment combines the functionalities of the previously described embodiments using respectively time-spread and spatially-spread beam conversion configurations. If the scanning system 100 is idle in a position that directs the beam 103 such that the vector 106 is aligned with the axis 82 (the angle 105 is zero), the beam conversion system 17 will behave in similar manner to the embodiment described in FIG. 7A. On the other hand, if the scanning system 100 rotates the beam 103 in a circular or spiral motion pattern around the axis 82, the result produced by the beam conversion system is similar to that described in the embodiment illustrated in FIG. 2B, having a rotating element.

As the beam 104 rotates in a circular pattern around the axis 82, the beam 91A, a center of which is illustrated by vector 87A, creates a circle of radius R on the surface 26 around the symmetry axis 82. The angle 97A is the angle of incidence between the vector 87A and the normal to the surface 26.

The beam 91A penetrates the surface 26, to create a refracted beam 92A, a center of which is defined by a vector 93A. An angle between the vector 93A and the normal to the surface 26 is a refraction angle 98. Due to scattering effect, the refracted beam 92 may be moderately divergent.

The center of beam 92 crosses the symmetry axis 82 at a target point N, which is located at the depth of D below the surface 26. The target point N will be continuously exposed to radiation and therefore will receive a maximum thermal doze. The target point N therefore defines the thermal center of the target volume 46. The shape and the size of the target volume 46 mostly depend on the diameter of the laser beam, the cross section power distribution of the beam, the refraction angle 98A and the scattering and absorption effect of the tissue. Due to geometric considerations, the thermal exposure will be symmetrically distributed around the symmetry axis 82, while the maximum thermal energy will normally be at target point N.

The angles 105, 85A, 96A, 94 and 97A and the distances A1 and C1 are all known by design. The refraction index for variety of materials is known in the art. Therefore, the distance D can be calculated using simple trigonometry laws.

By varying the angle 105, we can manipulate the distance R and the distance D. Alternatively, we can alter any of the: angle 94, distances A1 or distance C1 in order to manipulate the distance R and the distance D. Moreover, instead of causing the beam 105 rotate in a circular pattern around the axis 82, the system 100 is capable of producing a variety of geometric forms around the axis 82. That may include elliptical or even rectangular forms or discrete steps instead of continuous motion. All those manipulations allow producing the target volumes 46 of a various shapes, sizes, depths and energy distribution required for a specific application. These manipulations can be performed either between treatments, or even during the course of a single excitation pulse.

Figure 8B:
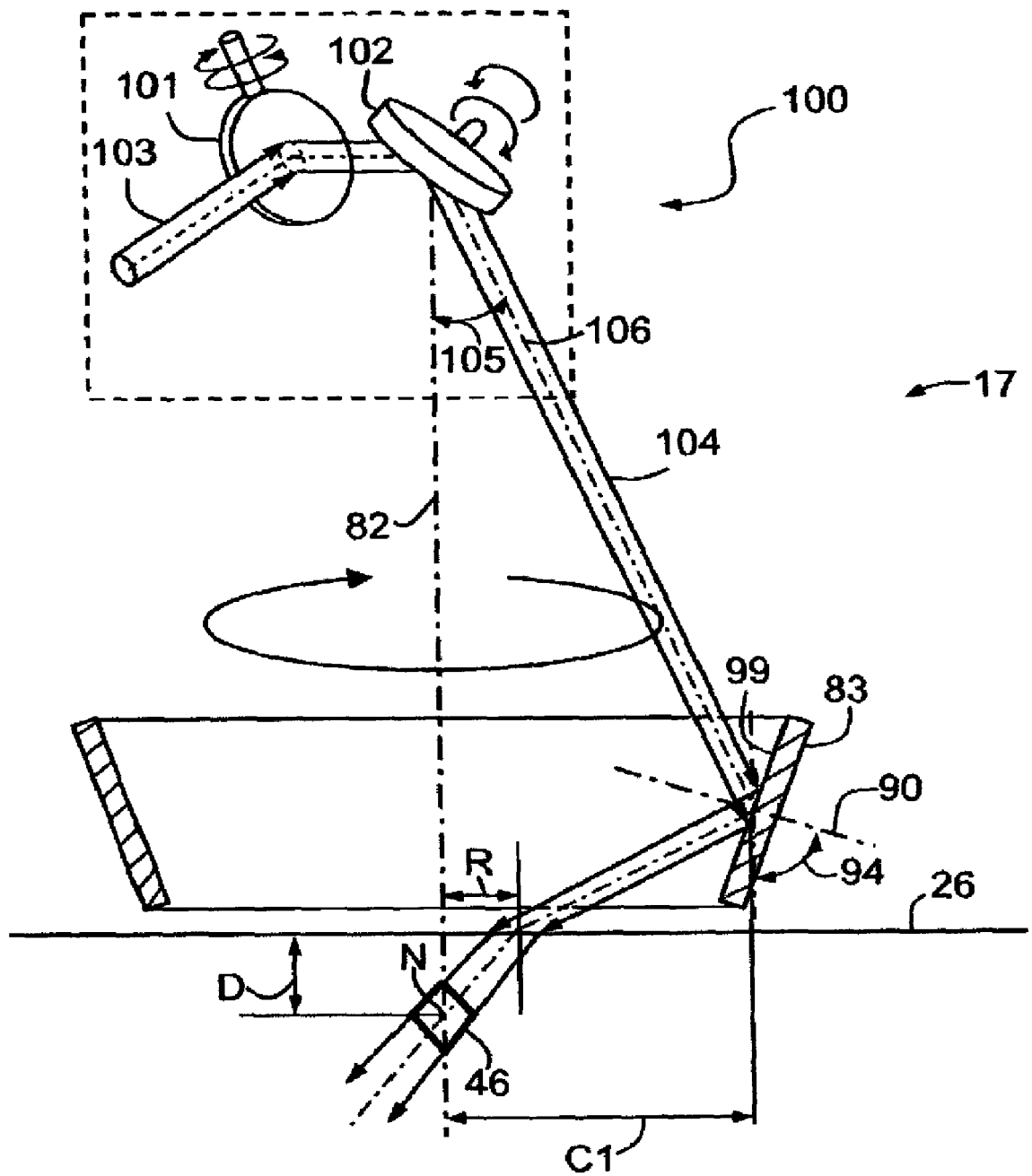
FIG. 8B illustrates a combination of schematic and perspective view of still another embodiment of the beam conversion system incorporating the principles of the invention.

An example of an additional preferred embodiment, utilizing the scanning system 100, but without the right angular cone 84, is illustrated in FIG. 8B.

It should be appreciated that these embodiments of the present invention can also be practiced using reflectors in a variety of geometric forms and configurations.

Figure 9:
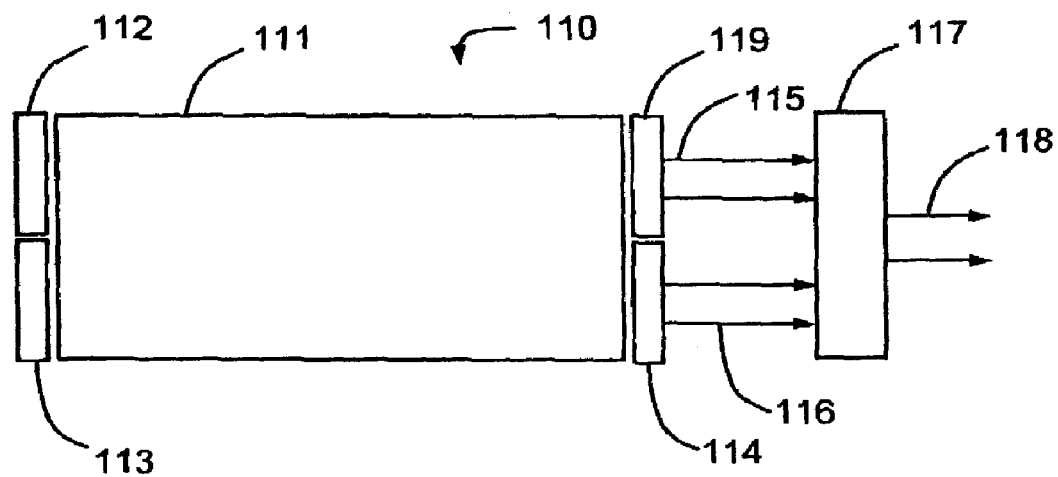
FIG. 9 illustrates a schematic view of a dual wavelength laser source incorporating the principles of the invention.

Another aspect of present invention is the simultaneous thermal treatment of multiple confine target volumes, preferably with different wavelengths and preferably with different pulse durations. Such configurations utilize a radiation source that can produce a beam with multiple wavelengths. An example of such a laser is a dual wavelength Nd:YAG laser. In one embodiment of the present invention, the radiation source 16 of FIG. 1C is a multiple wavelength laser 110, as depicted in FIG. 9. Flash pumped Nd:YAG lasers can be operated at both 1064 and 1320 nm. By coating the flat ends of a crystal 111 of typical size of 150 mm length and 8 mm diameter with a 1064 nm partial reflector 114 and 1320 nm partial reflector 119, as well as by using a 1064 total reflector 113 and 1320 nm total reflector 112, the laser can simultaneously emit a 1064 nm beam 116 and a 1320 nm beam 115. A beam combiner 117 enables the emission of a combined 1064 and 1320 nm beam 118. The pulse duration of the beam depends on the duration of the pumping flash-lamp and is typically between 1 millisecond to 300 milliseconds. Typical energy density at each wavelength may be 10-3000 Joules/cm2. A dual wavelength Nd:YAG laser may also be produced by the utilization of two rods, each rod coated for different wavelengths.

In another preferred embodiment of the present invention, a very high intensity array of diode lasers at different wavelengths (such as 755 nm and 810 nm) may be used. The lasers are operated with different pulse durations by varying the current pulse duration generated by the power supply.

Figure 10A:
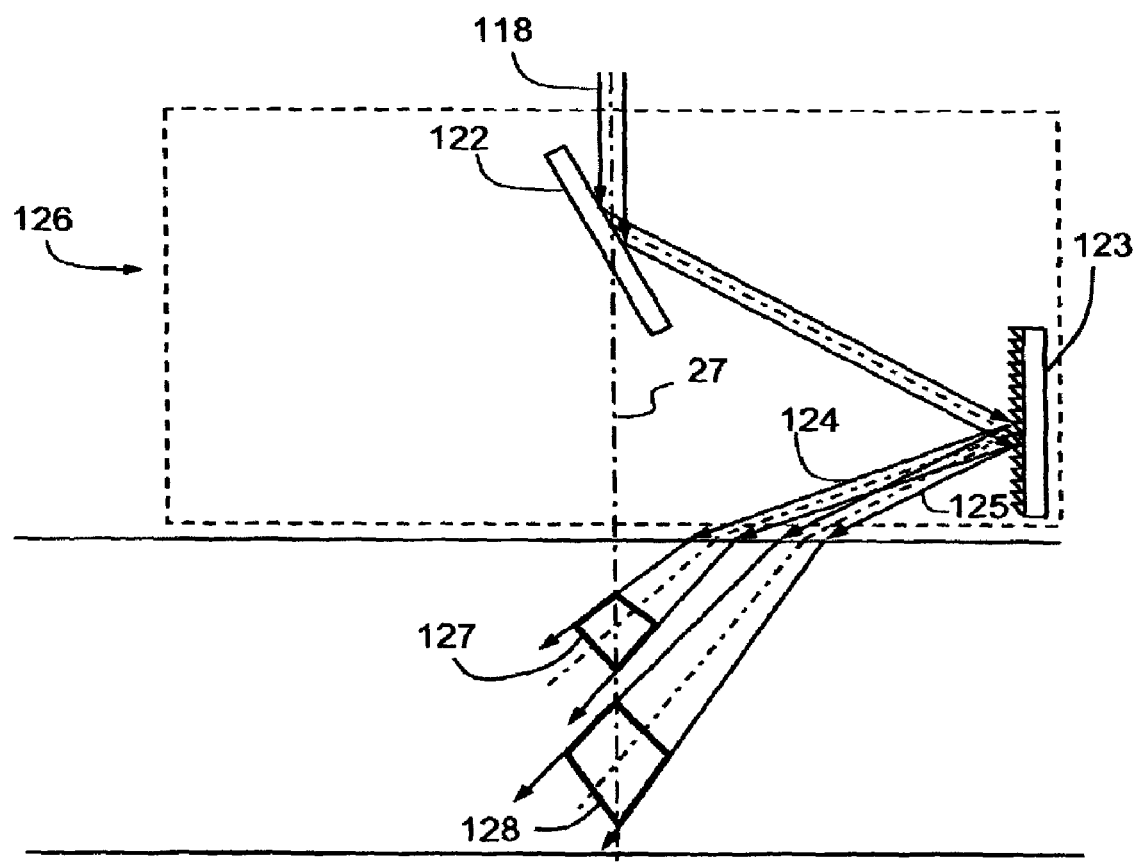
FIG. 10A shows a cross section of another embodiment of the beam conversion system incorporating the principles of the invention.

Reference is now made to FIG. 10A which shows one preferred method of implementing this dual wavelength embodiment of the present invention. During the excitation mode, a generally collimated, dual wavelength laser beam 118, such as one produced by multi-spectral laser 110, as depicted in FIG. 9, hits a mirror 122 from which it is directed to a reflective optical grating 123, which separates the two wavelengths and reflects the first beam 124 having first wavelength at first dispersion angle and the second beam 125 having a second wavelength at a second dispersion angle. By combining the mirror 122 and the optical grating 123 into a rotating unit 126 that rotates around the rotation axis 27, two scanning beams are generated, which simultaneously treat the target volume 127 with the beam 124 of the first wavelength and the target volume 128 with the beam 125 of the second wavelength.

The confined target volume 127 and the confined target volume 128 are vertically separated and treated with separate wavelengths, optimized for the required application. The angular rotation speed of the rotating unit 126 and the duration of the excitation time of the laser beam 118 are optimized to treat the specific lesions. Separate treatment times can be provided to each volume by exposure of each volume to a pulse with different duration. For example, at a speed of 6000 revolutions per minute (corresponding to a full circle scanning time of 10 ms), the target volume 127 could be treated with a 10 ms pulse, which corresponds to one rotation time, while the target volume 128 could be treated with a 50 ms pulse, which corresponds to 5 full rotations.

Figure 10B:
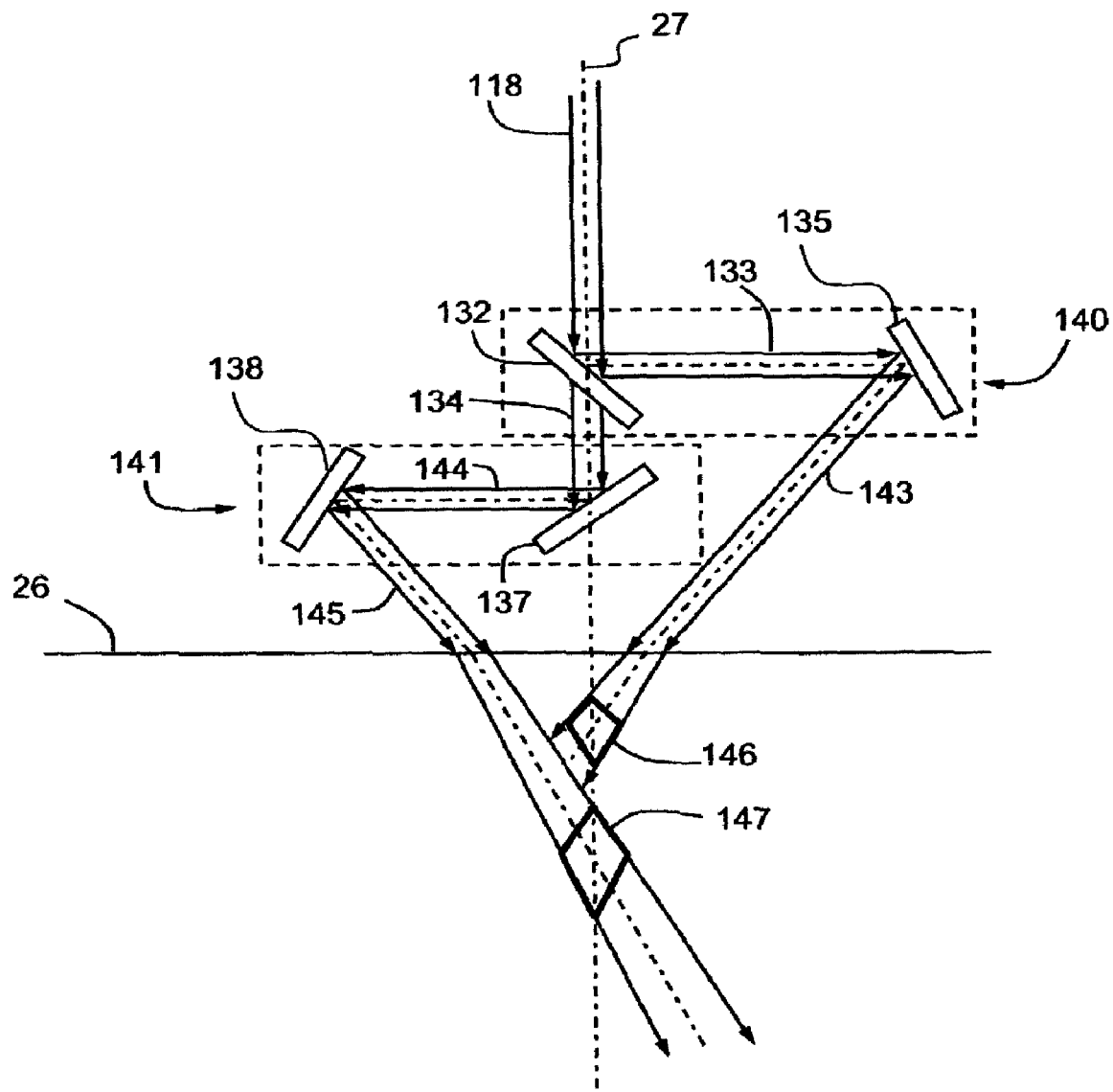
FIG. 10B shows a cross section of yet another embodiment of the beam conversion system incorporating the principles of the invention.

Reference is now made to FIG. 10B which shows a schematic representation of another preferred embodiment of the present invention, which provides additional temporal discrimination by excitation of dual wavelength laser beam 118 emitted by the laser at different wavelengths with different pulse durations. This is achieved, for example, by electronically controlling an intracavity laser shutter. A dichroic mirror 132 reflects beam 133 having wavelength lambda 1 and transmits beam 134 having wavelength lambda 2. The beam 133 is reflected from the mirror 135 and becomes beam 143 which is targeted to treat the confined volume target 146. The beam 134, reflected from mirror 137, becomes beam 144 which reflects from mirror 138 and is targeted to treat the confined volume target 147.

By combining the pair of mirrors 132 and 135 into a rotating unit 140 and the pair of mirrors 137 and 138 into a rotating unit 141, and by rotating the units 140 and 141 around the rotation axis 27, two scanning beams are generated, which simultaneously treat two target volumes under the surface 26. The target volume 146 is targeted by beam 143 while the target volume 147 is targeted by beam 145.

According to another preferred embodiment, the beam 118 is a single wavelength beam, such as 1064 nm, and the dichroic mirror 132 is substituted with a partial beam splitter which reflects part of the energy while the rest of the energy passes through. In such a case, target volumes 146 and 147 can be treated simultaneously with each receiving a predetermined optimal amount of energy.

An electronic angular position control of the mirrors 132, 135, 137 and 138 enables the variation of the depth of each of the treated volumes. It is possible to provide an electronically controlled shutter inside the cavity, thereby further controlling the temporal emissions of the beams, which hit the vertically separated target volumes.

In another embodiment, the dual wavelength laser beam is applied to the beam conversion system of any of the FIGS. 7A, 7B, 8A and 8B in which the reflecting surface 99 is replaced by a reflective optical grating 123, which separates the two wavelengths and allows treating two separate target volumes simultaneously.

For the purpose of this disclosure, the "target volume" is understood to mean a single volume that receives the thermal dose without repositioning target point N (or target point K in some embodiments). The "target zone" is understood to mean a plurality of target volumes all sharing a common axis 27 (or axis 82 is some drawings). The "treatment area" is understood to mean the region of the tissue that needs to be treated, preferably by creating a plurality of target zones.

In accordance with the principal of present invention and it different embodiments, after the a desired thermal effect is achieved in a required target zone, the target point N (or K in some embodiments) can be repositioned to a new treatment location on the surface of the tissue to produce new target volumes that form a new target zone. This could preferably be achieved by horizontal and angular (changing the angle between the axis and the normal to surface 26) repositioning of the axis 27 (or axis 82 is some embodiments). Therefore, by multiple repositioning of the axis 27 in discrete or continuous manner, any desired, treatment paths on the surface 26 can be created, covering the treatment area to suit a specific application.

In another preferred embodiment, the reposition of axis 27 is achieved by repositioning the beam conversion system, which could be accomplished manually by repositioning the treatment head.

In another embodiment, instead of manual repositioning of the treatment head, a mechanical two-dimensional positioning system known in art such as the one from Arrick Robotics Inc., can be included in the treatment head for scanning the treatment area.

In another embodiment, a plurality of treatment heads are provided in a form of two-dimensional matrix for treating larger treatment areas in simultaneous or in sequential manner.

Figure 5B:
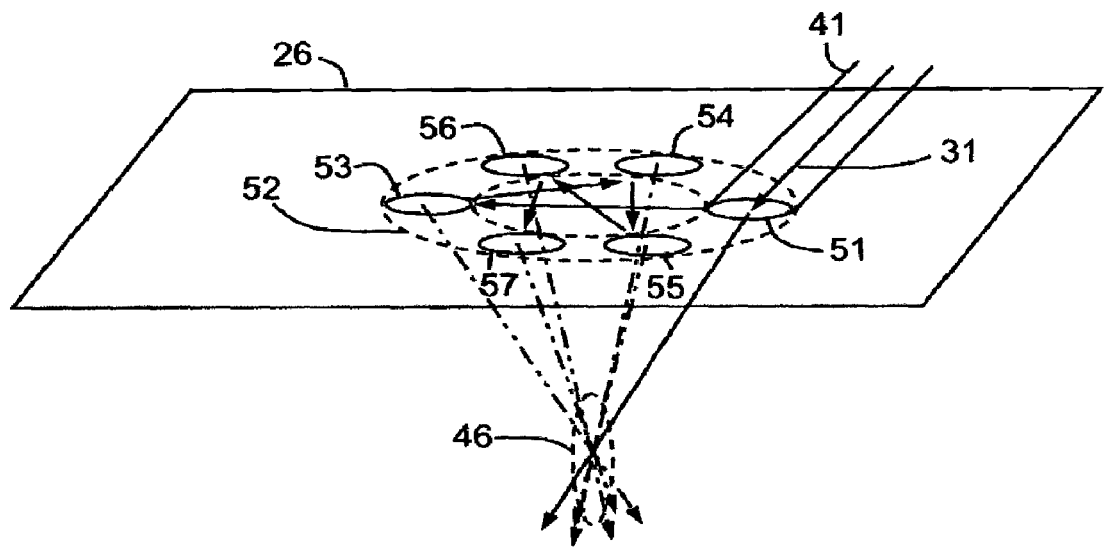
FIG. 5B shows a perspective view of an alternative projection of the light beam on the surface in accordance with the principals of the present invention.

FIG. 5B illustrates another preferred embodiment at which instead of producing the disk 52 of FIG. 5A in a continuous motion, the spot 51 is scanned over the surface 26 in a series of discrete steps. The beam 41, which is represented by vector 31, is initially positioned to produce a spot 51. Thereafter, the beam 41 is repositioned to produce a plurality of spots schematically exemplified by spots 53, 54, 55, 56 and 57 and consequently produce the target volume 46. In one embodiment, in order to reduce the accumulated heat in the superficial layer of the skin and to minimize the pain sensation, the locations 51, 53, 54, 55, 56 and 57 are arranged to be not adjacent to each other.

Figure 5C:
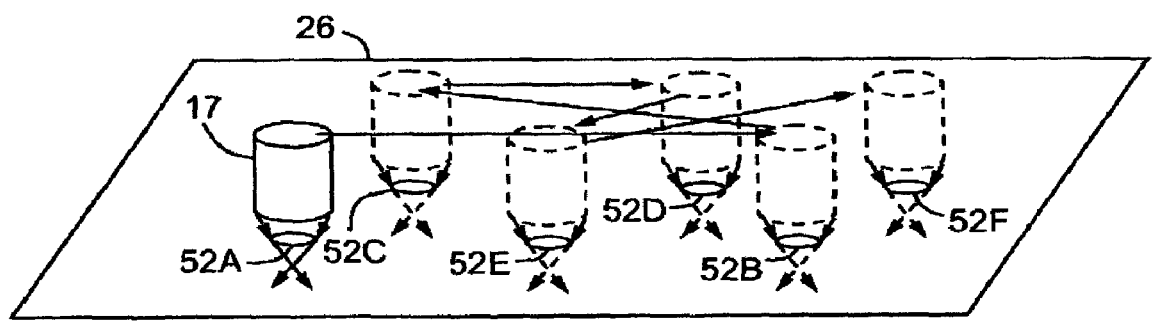
FIG. 5C shows a perspective view of a treatment pattern on the surface in accordance with the principals of present invention.

FIG. 5C illustrates another method of use, in which instead of producing the treatment area in a continuous motion, the surface 26 is scanned in a series of discrete steps. The beam conversion system 17 is initially positioned to produce the disk 52A. Thereafter, the beam conversion system 17 is repositioned to produce a plurality of disks schematically exemplified by disks 52B, 52C, 52D, 52E and 52F and consequently produce the target volumes (not shown) under each of those disks using the principles of present invention and exemplified earlier.

In one embodiment, in order to reduce the accumulated heat in the superficial layer of the skin and to minimize the pain sensation, the locations 51A, 52B, 52C, 52D, 52E and 52F are arranged to be not adjacent to each other.

Any of the above embodiments of the present invention can be performed using sources of energy such as radiofrequency (RF), microwave, ultrasound or other electromagnetic radiation applied in combination with the light energy. One particular advantage of the present invention when operated in combination with the RF, is in the manipulation of the RF electrical conductivity of the tissue by optical preheating of a confined target volume under the tissue surface.

The present invention can be practiced alone or with improvements known in the art, such as optical tracking system for controlling the treatment location, application of gel to the skin in order to reduce light scattering resulted from irregularities in the skin, use of an aiming beam for marking the treatment area, cooling before and/or during treatment, and imaging devices for visualization of the treatment target.

Applications

The present invention can be utilized in a variety of medical and aesthetic applications. Following are several examples that illustrate some of those applications.

EXAMPLE 1

An Application for Removing Wrinkles

Removing wrinkles in accordance with present invention includes delivering a beam of laser or incoherent radiation capable of causing sufficient thermal injury in the dermal region of the skin. The thermal injury elicits a healing response, which causes the skin to remodel itself, resulting in substantially less wrinkled skin. In particular, thermal injury causes partial denaturation of the collagen fibers in the targeted dermal region of skin. In one embodiment of present invention, the radiation directed to partially denature collagen in the dermis while reducing the thermal damage to the epidermis and upper layers of the dermis. As a result, a subject treated using the method of the present invention will have lessened wrinkles without damage to the epidermis.

Light penetration depth is a function of wavelength of the light source. A wavelength in the range of 800 to 1900 nm is appropriate in order to achieve deep collagen heating. Preferably, the wavelength in the range of 570-800 nm is utilized for shallower collagen contraction.

The laser beam 86 (or beam 104 or beam 118 in various embodiments described herein) utilized for this application, preferably has a fluence of between about 10 and 3000 joules/cm2. For example, a 1064 nm Nd:YAG laser may be used, or a 1320 nm Nd:YAG laser or a 1500 nm Nd:Glass laser or a 1450 nm diode laser.

The treatment volume should be at a skin depth larger than 100 microns, and can be varied in the range of 0.1 to 4 mm, preferably in the range of 0.1 to 1.2 mm.

For the treatment of a wrinkle in accordance with the present invention, the treatment head is positioned on subject's skin containing the wrinkle. The target point N is aimed at a depth of about 750 microns. The targeted dermal region is then irradiated with radiation pulses exiting from the treatment head 12 until collagen in that region receives the desired thermal doze. To accomplish this, the collagen at the selected depth in the targeted dermal region is preferably heated to a temperature in the range of about 50 to 70 degrees Celsius.

In another detailed embodiment, the region of skin including the wrinkle is stretched along the wrinkle before the beam of radiation is directed to the targeted dermal region below the wrinkle. Stretching the skin along the wrinkle before irradiating the skin causes partial denaturation of the collagen fibers across the wrinkle, while not damaging the fibers along the wrinkle. Partially denaturing the fibers across the wrinkle tightens the skin sufficiently to cause the wrinkle to disappear.

The present invention can also be utilized for shallow, ablative treatment of the papillary dermis that is located at the depth of approximately 0.1-0.3 mm. By positioning the target volume at the depth of the papillary dermis, it is possible to ablate the papillary dermis without vaporizing the epidermis. A variety of wavelengths, preferably in the infrared range, may be utilized for such purpose, including wavelength produced by Erbium, Holmium or CO2 lasers. For example, a low power (10 watts) CO2 lasers may be utilized with a 1 ms pulse.

EXAMPLE 2

An Application for Treating Sagging and Folded Skin

Sagging and folded skin may be reduced by a mechanism that involves shrinking collagen with heating. The thickness of the heated collagen influences the efficiency of the treatment. In order to perform a successful treatment, light should penetrate through the epidermis and be absorbed in deep layer of the dermis. Consequently, the treatment volume should be at a depth larger than 100 microns, and can be varied in the range of 0.1 to 4 mm. A wide range of wavelengths in the range of 800 to 1900 nm is appropriate in order to achieve deep collagen heating. Generally, the radiation of laser beam 86 (or beam 104 or beam 118 in various embodiments described herein) utilized for this application, preferably has a fluence of between about 10 and 3000 joules/cm2.

For example, a 1064 nm Nd:YAG laser may be used, or a 1320 nm Nd:YAG laser or a 1500 nm Nd:Glass laser or a 1450 nm diode laser. It must be emphasized that laser beam with energy density as high as 500 joules/cm2 in prior art lasers are normally creating severe adverse effects to the skin surface such as epidermal burn. However, by utilizing the present invention, the skin surface is not damaged because the fluence on the skin surface may be lower than 50 joules/cm2. In this application, the collagen at the selected depth in the targeted dermal region is preferably heated to a temperature in the range of about 65 to 85 degrees Celsius.

EXAMPLE 3

An Application for Removing Unwanted Hair

In another embodiment, the present invention is utilized to remove unwanted hair. In accordance with one embodiment of present invention, the target volume could be positioned at a selected depth which can be varied in the range of 0.1 to 4 mm along the hair follicle, thereby applying thermal energy necessary for permanent or substantially permanent hair removal.

For example, by positioning the target volume generally concentric with the bulge or the papilla maximum thermal energy is delivered into the areas believed to contain the cells responsible for hair growth, thus promoting permanent or long-term hair removal. Unlike other methods, the present invention allows delivering sufficient amount of energy without damaging the epidermis. Furthermore, the heating of each hair follicle is done directly and not through heat dissipation from the hair shaft as in some other methods.

Additionally, unlike other methods based solely on selective photothermolysis, the present invention allows using wavelengths, which are less absorbed by the skin melanin, penetrate deeper and allow treating darker skin patients. Furthermore, the substantially reduced fluence applied to epidermis in accordance with present invention may allow treating even completely dark skin patients. Moreover, the melanin in the hair need not be targeted. However, if melanin is the targeted chromophor, only small amount of such chromophor is required to produce the desired thermal effect. As a result, gray and blond hair can be treated.

A wavelength in the range of 570 to 1100 nm is appropriate in order to reach the predetermined depth. For example, a 1064 nm Nd:YAG laser may be used.

The laser beam 86 (or beam 104 or beam 118 in various embodiments described herein) utilized for this application, preferably has a fluence of between about 10 and 3000 joules/cm2.

Figure 10C:
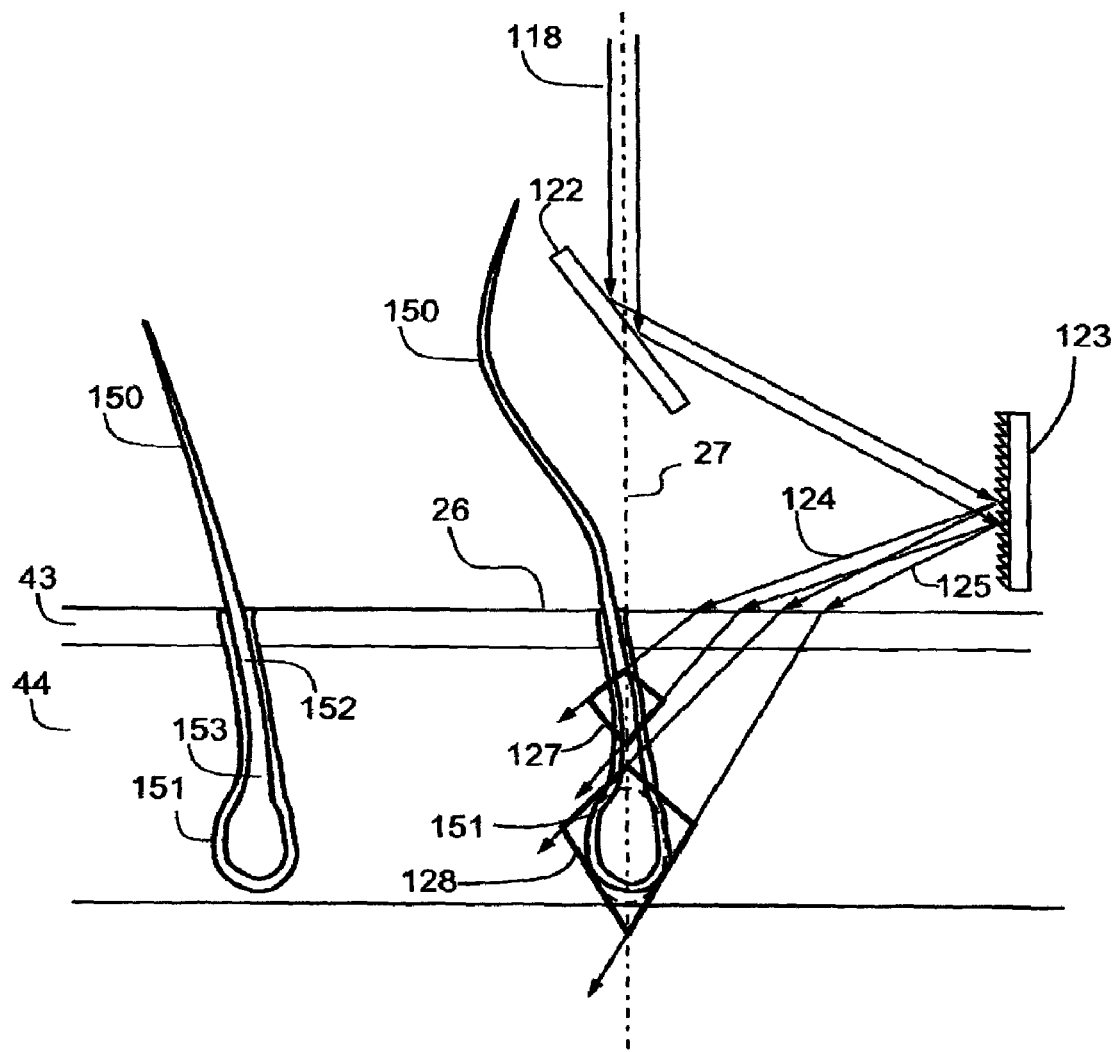
FIG. 10C shows a cross section of one embodiment beam conversion system incorporating the principles of the invention applied for hair treatment.

FIG. 10C illustrates an example of the beam conversion system of FIG. 10A, applied for treatment of hair. The hair consists of the hair shaft 150 that normally extends from the epidermis 43, a hair follicle 152 and hair root 153. The deepest and the thickest part of the hair is the bulb 151, which is normally located in the dermis 44 up to approximately 4 mm below the surface 26.

Two particular zones, the first near the shaft base (papilla); and the second approximately a third of the way down the shaft, known as the bulge, are believed to contain the cells responsible for hair growth. Direct heat absorption into these zones and damage to them via heating should lead to permanent hair removal or at least substantially delayed regrowth.

In this embodiment, the confined target volume 127 and the confined target volume 128 are positioned to simultaneously treat different subjacent depths of a hair follicle that are believed to be responsible for hair growth, with different optimal time durations. For example, the deeper part of the hair is treated with longer wavelength of 810-1100 nm and longer pulse duration, typically 30-300 ms, while the shallow part of the hair can be treated with shorter wavelengths, typically 600-900 nm and shorter pulses, typically 2-30 ms. Other embodiments of present invention can remove unwanted hair in similar manner.

EXAMPLE 4

An Application for Treating Varicose Veins

In another embodiment, the present invention is utilized to provide a method and apparatus for treatment of vascular disorders.

In general, the larger is the penetration depth and the higher is the energy delivered to the vessels wall, so more expanded is the heating of vessels wall to cover a larger percentage of the interior and also more of the vessel's walls. It is desirable therefore to use a high energy light for treating varicose veins, especially those that are larger and deeper. One significant side effect of increasing the energy level is a potential damage to the epidermis. A significant advantage of the present invention is in reduction of such damage.

Preferably, the thermal dose is sufficient to cause total obstruction of the venous lumen.

Usually, the size and the depth of the targeted vessels dictate the effective pulse duration and total fluence. The pulse duration should ideally be closely matched to the thermal relaxation time of the vessels, which is a function of the vessels size. Generally, for the treatment of the vessels such as varicose veins, a total effective pulse durations of greater than a millisecond are desirable, with 5 milliseconds to 100 milliseconds being preferred in the case of larger vessels.

Over the course of the pulse duration, the fluence should be high enough to raise the temperature of the walls of the vessel to a temperature at which their constituent proteins will denature. Preferably, a temperature of 70 degrees Celsius is an accepted target.

The laser beam 86 (or beam 104 or beam 118 in various embodiments described herein) utilized for this application, preferably has a fluence of between about 10 and 3000 joules/cm2. For deep lying and/or larger vessels the desirable wavelength range is the near-infrared. For example, a 1064 nm Nd:YAG laser, with 100 ms pulse duration, may be used.

LIST OF APPLICATIONS

In addition to several specific application described in details above, the present invention is utilized to provide a method and apparatus for treating many dermatological disorders including but not limited to wrinkles, stretch marks, vascular disorders, hair removal, treatment of PFB, treatment of acne or chicken pox scars or other scars in the skin, treating cellulite, elimination of pigmented lesions and tattoos, treatment of psoriasis, skin resurfacing as well as non-ablative photorejuvenation, treatment of various skin tumors. The present invention may also be used to treat intradermal parasites such as larva migrans as well as to treat fungus nails and various other conditions which may exist in the patient's body at depths of less than approximately 4 mm.

Additional applications related to thermal shrinking of the collagen that may include non-surgical treatment of aesthetic disorders related to sagging or folding skin such as mild breast ptosis, nasolabial folds, drooping jowls, eyelids, saggy arms, abdomen and thighs as well as other body sites.

The present invention is not limited to the treatment of dermatological problems. The method is useful in many additional applications that require treating deeper layers of the tissue while sparing the overlying superficial layers. Therefore, in is still another specific embodiment, the present invention is utilized to provide a method and apparatus for treatment of non-dermal tissues. That includes sub-surface ablation and coagulation of tissue for example during open or laparoscopic surgery as well as other minimally invasive procedures. The treatment head can be miniaturized to fit laparoscopic equipment or a catheter and to be used for a variety of medical conditions.

While the present invention has been particularly shown and described with reference to specific embodiments, it should be understood by those skilled in the art that various changes in form and detail may be made therein without departing from the spirit and scope of the present invention as defined by the appended claims.

Accordingly, modifications such as those suggested above, but not limited thereto, are to be considered within the scope of the present invention.

The invention claimed is:

1. Apparatus for delivering radiation to a target volume (46) beneath a skin surface, comprising:
a radiation source (16) for inputting a beam of said radiation having an input energy fluence; and
a beam conversion system (17) comprising:
a rotator (21) having a rotation axis in optical alignment with said beam and a first radiation directing element (24) arranged in optical communication with said radiation source comprising a reflective element rigidly mounted on said rotator having a symmetry axis (27), collinear with said rotation axis for rotating said input beam around said symmetry axis said first radiation directing element adapted to direct said beam in a plurality of directions spaced around said symmetry axis, and
a second radiation directing element (25) comprising a single reflective element mounted at a fixed distance from said rotation axis facing said first radiation directing element for redirecting said directed beam through said surface radially inwards towards said symmetry axis onto said at least one target volume (46) disposed on said symmetry axis beneath said skin surface, such that said radiation is spread out in a rotational path on said surface, wherein
said rotator is adapted to direct said beam in directions such that any given point of said target volume is exposed to said radiation during the entire energy excitation period of said beam, while any given point of said rotational path on said surface is exposed to said radiation only during portion of said enemy excitation period, and said first radiation directing element (24A) has reflecting surface with curvature in at most, one plane, and said second radiation directing element (25) has reflecting surface (39) with curvature in at most, one plane, and none of said radiation impinging on said skin surface overlaps with said symmetry axis, and said energy fluence of said radiation at said target volume is higher than said energy fluence of said radiation at said skin surface.

2. The apparatus according to claim 1 wherein said second radiation directing element is rigidly mounted on said rotator and is rigidly coupled to said first radiation directing element.

3. The apparatus according to claim 1 wherein said radiation has a spectral band between 300 nm and 11000 nm.

4. The apparatus according to claim 1, said first radiation directing element and said second radiation directing element are selected such that said energy fluence of said redirected beam is less than or equal to said energy fluence of said input beam.

5. The apparatus according to claim 1, said first radiation directing element and said second radiation directing element are selected such that the focal point of such beam is located beyond said target volume.

6. The apparatus according to claim 1 wherein said redirected radiation is in a collimated form.

7. The apparatus according to claim 1 wherein said beam conversion system converges said radiation onto said target volume without the use of elements having optical power.

8. The apparatus according to claim 1 wherein said second radiation directing element converges said radiation onto said target volume without the use of elements having optical power.

9. The apparatus according to claim 1 wherein said period of said rotation is shorter than or equal to the duration of said energy excitation period.

10. The apparatus according to claim 1 wherein said energy excitation period is a multiple of said period of said rotation.

11. The apparatus according to claim 1 wherein said energy excitation period is from 1 millisecond to 300 milliseconds.

12. A method for delivering radiation beneath a skin surface, comprising the steps of:

providing a radiation source for inputting a beam of said radiation having an input energy fluence; and providing a rotator having a rotation axis in optical alignment with said beam; and providing a first radiation directing element arranged in optical communication with said radiation source comprising a reflective element rigidly mounted on said rotator having a symmetry axis, collinear with said rotation axis for rotating said input beam around said symmetry axis said first radiation directing element adapted to direct said beam in a plurality of directions spaced around said symmetry axis; and providing a second radiation directing element comprising a single reflective element mounted at a fixed distance from said rotation axis facing said first radiation directing element for redirecting said directed beam through said surface radially inwards towards said symmetry axis onto said at least one target volume disposed on said symmetry axis beneath said skin surface, such that said radiation is spread out in a rotational path on said surface, wherein any given point of said target volume is exposed to said radiation during the entire energy excitation period of said beam, while any given point of said rotational path on said surface is exposed to said radiation only during portion of said energy excitation period, and said first radiation directing element has reflecting surface with curvature in at most, one plane, and said second radiation directing element has reflecting surface with curvature in at most, one plane, and none of said radiation impinging on said skin surface overlaps with said symmetry axis, and said energy fluence of said radiation at said target volume is higher than said energy fluence of said radiation at said skin surface.

13. A method according to claim 12 and further comprising the step of providing a second reflective element rigidly mounted on said rotator and rigidly coupled to said first radiation directing element for rotating said input radiation around said symmetry axis, such that said radiation is spread out in a rotational path on said surface.

14. A method according to claim 12 and further comprising the step of providing a first radiation directing element and a second radiation directing element for converging said radiation onto said target volume without the use of elements having optical power.

15. A method according to claim 12 and further comprising the step of providing a first radiation directing element and a second radiation directing element wherein said radiation is non-focused at said target volume.

16. A method according to claim 13 and wherein said rotated radiation is in a generally collimated form.

17. A method according to claim 12, and further comprising the step of providing a first radiation directing element and a second radiation directing element wherein said energy fluence of said redirected beam is less than or equal to said energy fluence of said input beam.

* * * * *